US012583124B2

(12) United States Patent　　(10) Patent No.:　US 12,583,124 B2
Wu et al.　　(45) Date of Patent:　Mar. 24, 2026

(54) METHODS AND SYSTEMS FOR POSITIONING ROBOTS AND ADJUSTING POSTURES

(71) Applicant: WUHAN UNITED IMAGING SURGICAL CO., LTD., Wuhan (CN)

(72) Inventors: Tong Wu, Wuhan (CN); Bo Wu, Wuhan (CN); Yong Deng, Wuhan (CN); Quanquan Wang, Wuhan (CN); Qin Huang, Wuhan (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 90 days.

(21) Appl. No.: 18/506,980

(22) Filed: Nov. 10, 2023

(65) Prior Publication Data

US 2024/0075631 A1　　Mar. 7, 2024

Related U.S. Application Data

(63) Continuation of application No. PCT/CN2022/092003, filed on May 10, 2022.

(30) Foreign Application Priority Data

May 10, 2021　(CN) .......................... 202110505732.6
Nov. 19, 2021　(CN) .......................... 202111400891.6

(51) Int. Cl.
　　B25J 9/16　　　(2006.01)
　　A61B 34/30　　(2016.01)
(52) U.S. Cl.
　　CPC ............. B25J 9/1697 (2013.01); B25J 9/163 (2013.01); B25J 9/1653 (2013.01); B25J 9/1664 (2013.01); *A61B 34/30* (2016.02)

(58) Field of Classification Search
　　CPC ........ B25J 9/1697; B25J 9/163; B25J 9/1653; B25J 9/1664; B25J 9/1656; B25J 13/089;
(Continued)

(56) References Cited

U.S. PATENT DOCUMENTS

2016/0379042 A1 * 12/2016 Bourlai ................ G06V 40/171
　　　　　　　　　　　　　　　　　382/118
2017/0155829 A1　6/2017　Wang et al.
(Continued)

FOREIGN PATENT DOCUMENTS

CN　　103793915 B　　3/2017
CN　　108985257 A　　12/2018
(Continued)

OTHER PUBLICATIONS

The Extended European Search Report in European Application No. 22806750.0 mailed on Aug. 26, 2024, 7 pages.
(Continued)

*Primary Examiner* — Esvinder Singh
(74) *Attorney, Agent, or Firm* — METIS IP LLC

(57)　　　　ABSTRACT

Embodiments of the present disclosure provide a method and system for positioning a robot and adjusting a posture. The method may include obtaining a first image and a second image of a target object. The first image may be captured using an image capturing apparatus, and the second image may be captured using a medical imaging device. The method may also include determining at least one target region corresponding to at least one target portion of the target object from the first image. The at least one target portion may be less affected by physiological motions than other portions. The method may further include determining positioning information of the robot based on the at least one target region and the second image.

20 Claims, 16 Drawing Sheets

300

(58) Field of Classification Search
CPC ...... B25J 19/021; B25J 19/022; B25J 19/026; A61B 34/30; A61B 2034/105; A61B 90/361; A61B 2034/2065; A61B 2090/364; A61B 34/00; A61B 34/20; A61B 2034/2046; A61B 2034/2055; A61B 2034/2057; A61B 2034/2063; A61B 2034/2068; A61B 34/70; A61B 90/36; A61B 2090/367; A61B 2090/371; A61B 2090/3762; A61B 2090/378; A61B 2090/374; A61B 2090/376; G06V 10/759; G06V 10/82; G06V 40/16; G06V 40/165; G06V 40/168; G06V 40/171; G05B 2219/2652; G05B 2219/40082; G05B 2219/37092; G06T 7/74
See application file for complete search history.

(56) References Cited

U.S. PATENT DOCUMENTS

| | | |
|---|---|---|
| 2018/0185113 A1 | 7/2018 | Gregerson et al. |
| 2019/0046232 A1 | 2/2019 | Tokuda et al. |
| 2020/0242339 A1 | 7/2020 | Bustan et al. |
| 2020/0297228 A1* | 9/2020 | Crawford ................. A61B 5/24 |
| 2021/0100627 A1* | 4/2021 | Soper ................... G06T 7/0014 |
| 2021/0121250 A1 | 4/2021 | Uesugi |
| 2021/0196399 A1* | 7/2021 | Ayvali ................... A61B 34/30 |
| 2021/0244485 A1 | 8/2021 | Coiseur et al. |
| 2022/0022985 A1 | 1/2022 | Liu et al. |
| 2022/0061921 A1* | 3/2022 | Crawford ................. G06T 7/74 |
| 2022/0104878 A1* | 4/2022 | Weiss .................... G16H 20/40 |

| | | | | |
|---|---|---|---|---|
| 2022/0265373 A1* | 8/2022 | Kim | ...................... | A61B 34/32 |
| 2023/0012353 A1* | 1/2023 | Thienphrapa | ............ | A61B 8/12 |
| 2023/0410453 A1* | 12/2023 | Zeng | ...................... | G06T 19/20 |

FOREIGN PATENT DOCUMENTS

| | | |
|---|---|---|
| CN | 105852970 B | 6/2019 |
| CN | 109859256 A | 6/2019 |
| CN | 110215284 A | 9/2019 |
| CN | 110266940 | 9/2019 |
| CN | 110377015 A | 10/2019 |
| CN | 110382046 A | 10/2019 |
| CN | 111862180 A | 10/2020 |
| CN | 111862299 A | 10/2020 |
| CN | 112022355 A | 12/2020 |
| CN | 112446917 | 3/2021 |
| CN | 113274130 A | 8/2021 |
| CN | 113379850 | 9/2021 |
| CN | 113397704 A | 9/2021 |
| CN | 114098980 A | 3/2022 |
| JP | 2005028468 A | 2/2005 |
| WO | 2016187985 | 12/2016 |
| WO | 2019074958 A1 | 4/2019 |
| WO | 2019196478 A1 | 10/2019 |

OTHER PUBLICATIONS

Chen, Guodong et al., Space Registration and Practice of a Brain Surgery Robot Based on Optical Localization, Chinese Journal of Scientific Instrument, 28(3): 499-503, 2007.
International Search Report in PCT/CN2022/092003 mailed on Aug. 12, 2022, 7 pages.
Written Opinion in PCT/CN2022/092003 mailed on Aug. 12, 2022, 10 pages.

* cited by examiner

<u>100</u>

<u>100</u>

300

400

500

600A

600B

<u>1000</u>

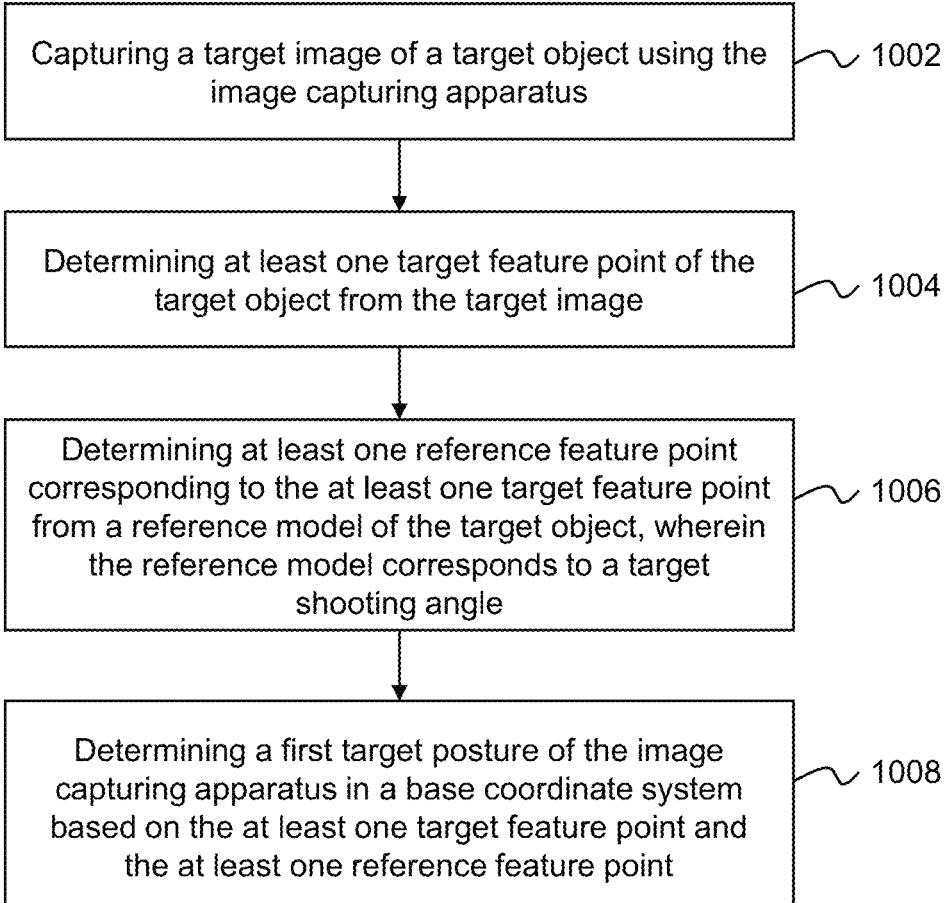

Capturing a target image of a target object using the image capturing apparatus    1002

Determining at least one target feature point of the target object from the target image    1004

Determining at least one reference feature point corresponding to the at least one target feature point from a reference model of the target object, wherein the reference model corresponds to a target shooting angle    1006

Determining a first target posture of the image capturing apparatus in a base coordinate system based on the at least one target feature point and the at least one reference feature point    1008

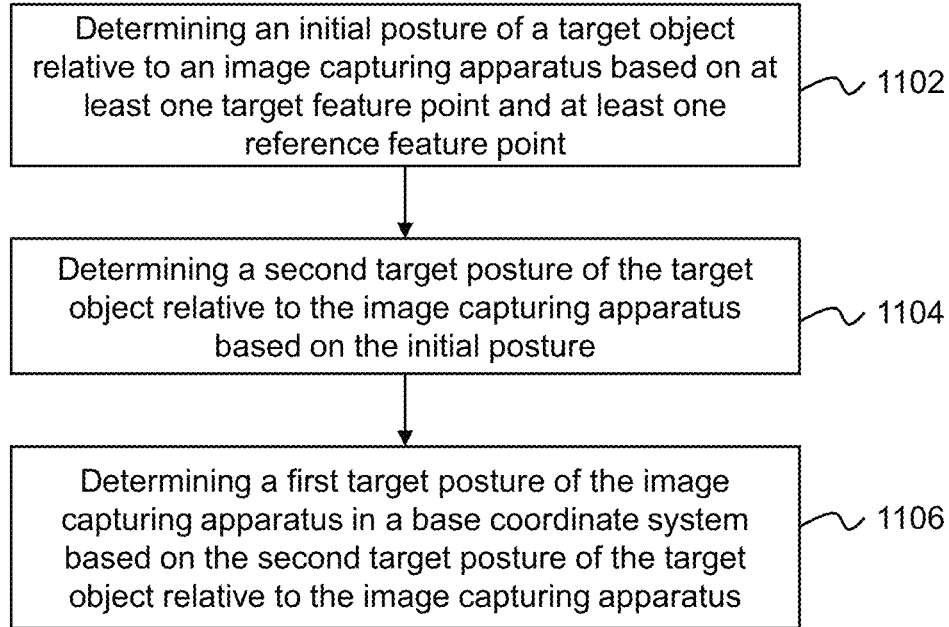

Determining an initial posture of a target object relative to an image capturing apparatus based on at least one target feature point and at least one reference feature point ~ 1102

Determining a second target posture of the target object relative to the image capturing apparatus based on the initial posture ~ 1104

Determining a first target posture of the image capturing apparatus in a base coordinate system based on the second target posture of the target object relative to the image capturing apparatus ~ 1106

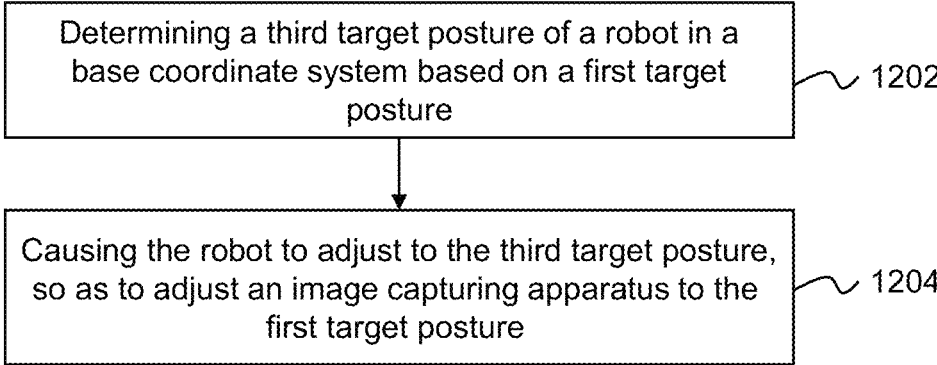

Determining a third target posture of a robot in a base coordinate system based on a first target posture ~ 1202

Causing the robot to adjust to the third target posture, so as to adjust an image capturing apparatus to the first target posture ~ 1204

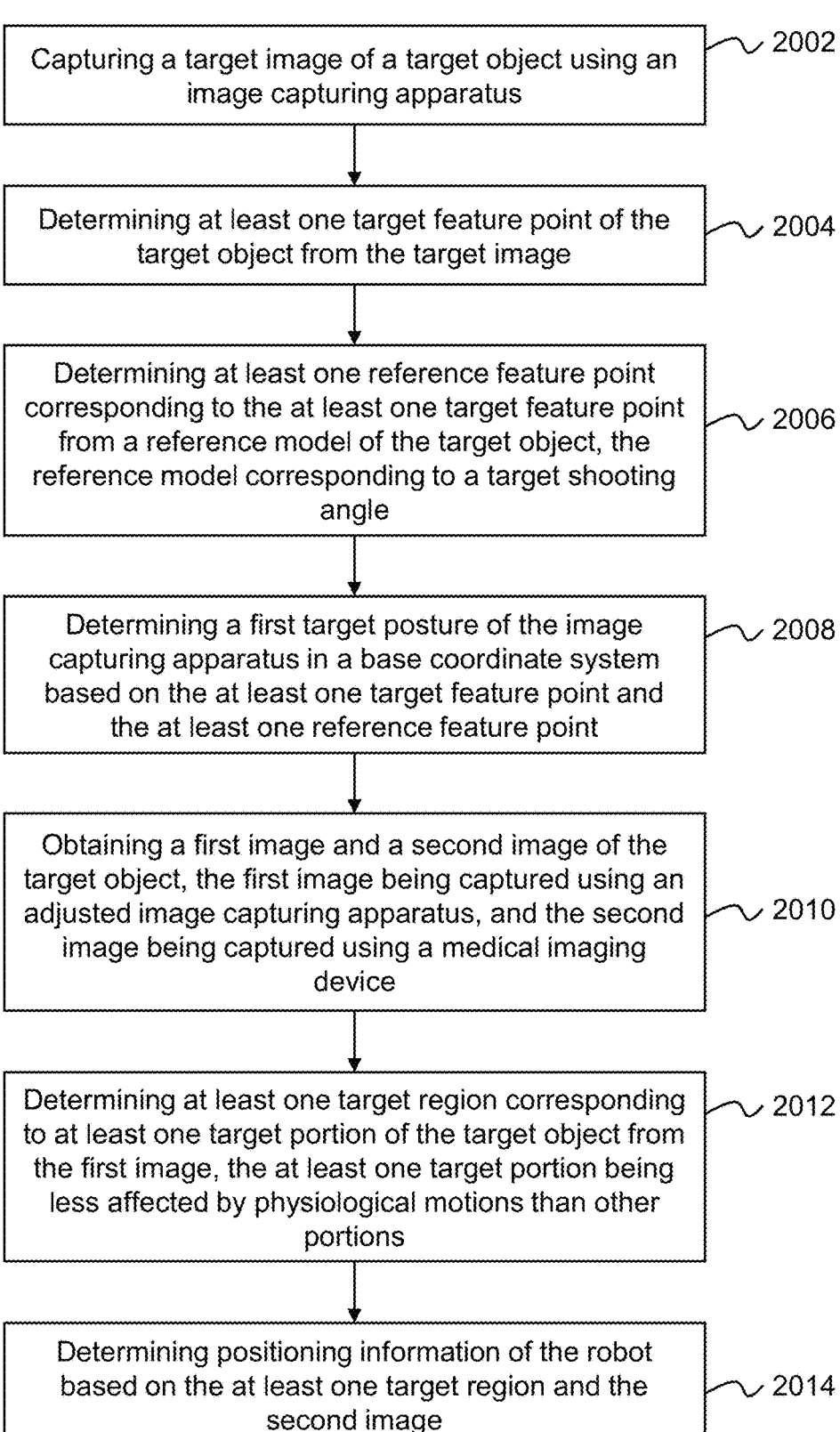

Capturing a target image of a target object using an image capturing apparatus — 2002

Determining at least one target feature point of the target object from the target image — 2004

Determining at least one reference feature point corresponding to the at least one target feature point from a reference model of the target object, the reference model corresponding to a target shooting angle — 2006

Determining a first target posture of the image capturing apparatus in a base coordinate system based on the at least one target feature point and the at least one reference feature point — 2008

Obtaining a first image and a second image of the target object, the first image being captured using an adjusted image capturing apparatus, and the second image being captured using a medical imaging device — 2010

Determining at least one target region corresponding to at least one target portion of the target object from the first image, the at least one target portion being less affected by physiological motions than other portions — 2012

Determining positioning information of the robot based on the at least one target region and the second image — 2014

METHODS AND SYSTEMS FOR POSITIONING ROBOTS AND ADJUSTING POSTURES

CROSS-REFERENCE TO RELATED APPLICATIONS

This application is a continuation of International Application No. PCT/CN2022/092003, filed on May 10, 2022, which claims priority to Chinese Patent Application No. 202110505732.6, filed on May 10, 2021, titled "METHODS, APPARATUS, SYSTEMS, AND COMPUTER DEVICES FOR POSITIONING ROBOTS," and Chinese Patent Application No. 202111400891.6, filed on Nov. 19, 2021, titled "METHODS, SYSTEMS, AND STORAGE MEDIA FOR ADJUSTING POSTURES OF CAMERAS AND SPATIAL REGISTRATION," the entire contents of each of which are hereby incorporated by reference.

TECHNICAL FIELD

The present disclosure relates to the field of robots, and in particular, to methods and systems for positioning robots and adjusting postures.

BACKGROUND

In recent years, robots are widely used in the medical field, such as orthopedics, neurosurgery, thoracoabdominal interventional surgeries or treatment, etc. Generally speaking, a robot includes a robotic arm with a multi-degree-of-freedom structure, which includes a base joint where a base of the robotic arm is located and an end joint where a flange of the robotic arm is located. The flange of the robotic arm is fixedly connected with end tools, such as surgical tools (e.g., electrode needles, puncture needles, syringes, ablation needles, etc.).

When the robots are used, it is necessary to precisely position the robots and adjust postures of the robots, such that preoperative planning and/or surgical operations can be performed accurately.

SUMMARY

One embodiment of the present disclosure provides a method for positioning a robot. The method may include obtaining a first image and a second image of a target object, the first image being captured using an image capturing apparatus, and the second image being captured using a medical imaging device; determining at least one target region corresponding to at least one target portion of the target object from the first image, wherein the at least one target portion is less affected by physiological motions than other portions; and determining positioning information of the robot based on the at least one target region and the second image.

One embodiment of the present disclosure provides a method for adjusting a posture of an image capturing apparatus. The method may include capturing a target image of a target object using the image capturing apparatus; determining at least one target feature point of the target object from the target image; determining at least one reference feature point corresponding to the at least one target feature point from a reference model of the target object, wherein the reference model corresponds to a target shooting angle; and determining a first target posture of the image capturing apparatus in a base coordinate system based on the at least one target feature point and the at least one reference feature point.

One embodiment of the present disclosure provides a system for positioning a robot. The system may include a storage device configured to store a computer instruction, and a processor connected to the storage device. When executing the computer instruction, the processor may cause the system to perform the following operations: obtaining a first image and a second image of a target object, the first image being captured using an image capturing apparatus, and the second image being captured using a medical imaging device; determining at least one target region corresponding to at least one target portion of the target object from the first image, wherein the at least one target portion is less affected by physiological motions than other portions; and determining positioning information of the robot based on the at least one target region and the second image.

BRIEF DESCRIPTION OF THE DRAWINGS

The present disclosure will be further illustrated by way of exemplary embodiments, which will be described in detail through the accompanying drawings. These embodiments are not limiting, and in these embodiments the same numbering indicates the same structure, wherein:

FIG. 10 is a flowchart illustrating an exemplary process for adjusting a posture of an image capturing apparatus according to some embodiments of the present disclosure;

3

Figure 13A:
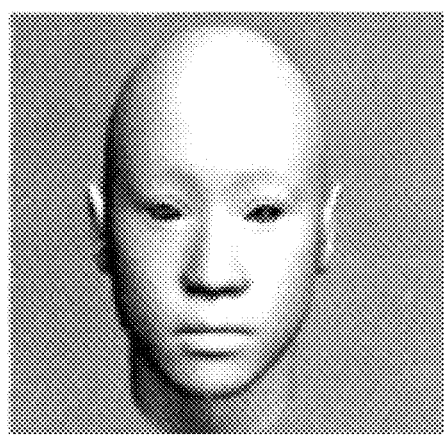
Figure 13B:
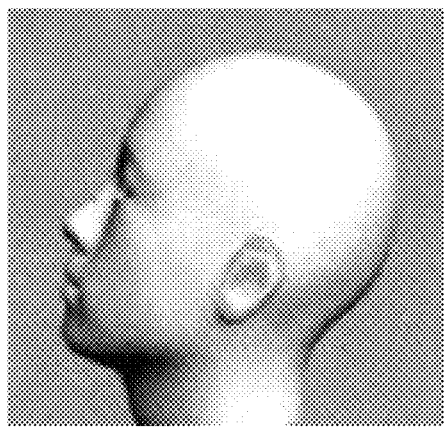
Figure 14:
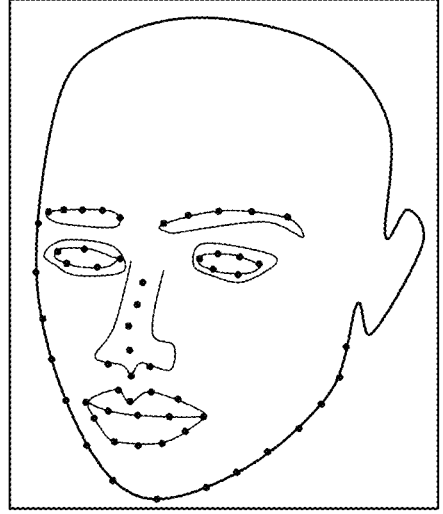
Figure 15A:
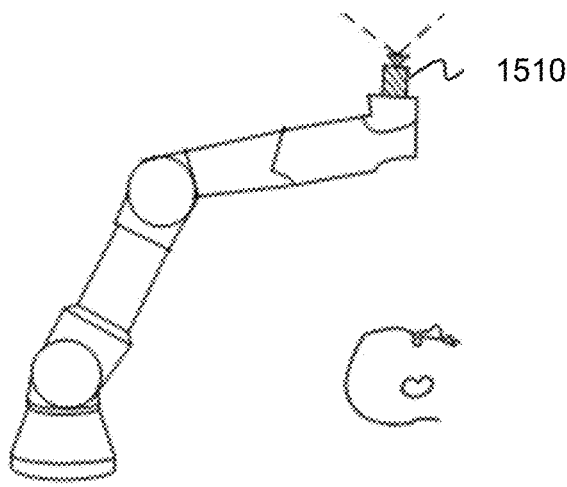
Figure 15B:
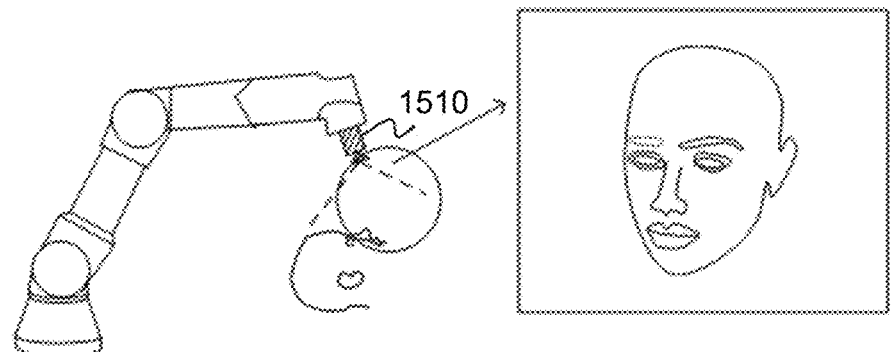
Figure 15C:
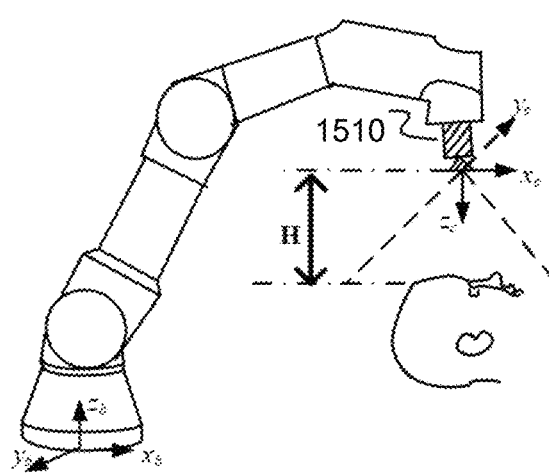
Figure 16A:
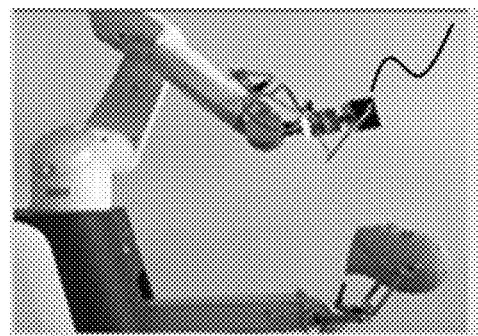
Figure 16B:
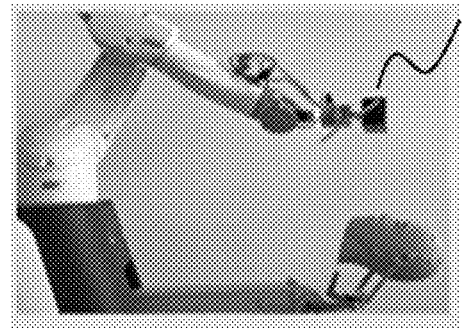
Figure 16C:
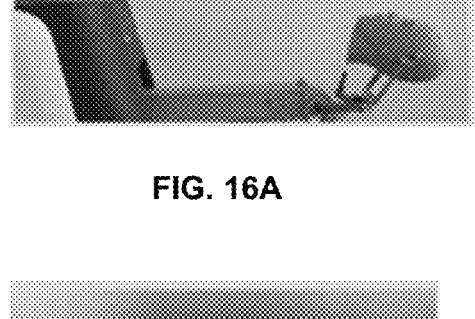
Figure 16D:
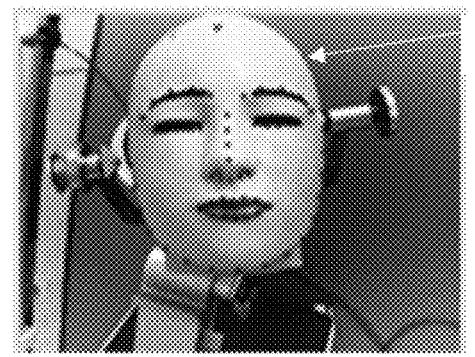
Figure 16E:
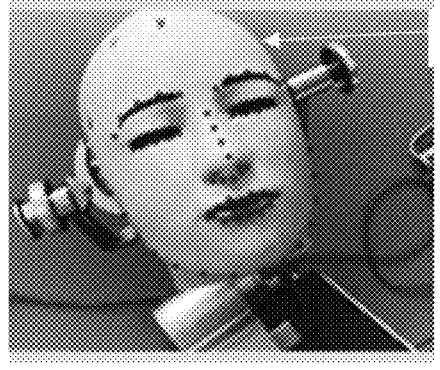
Figure 16F:
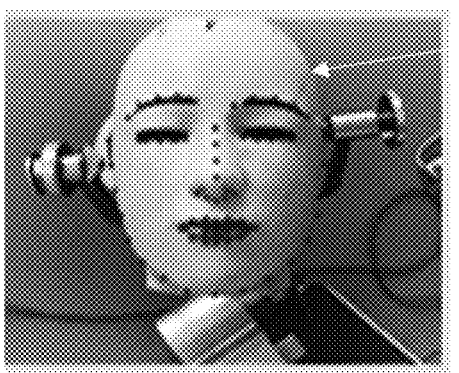
Figure 16G:
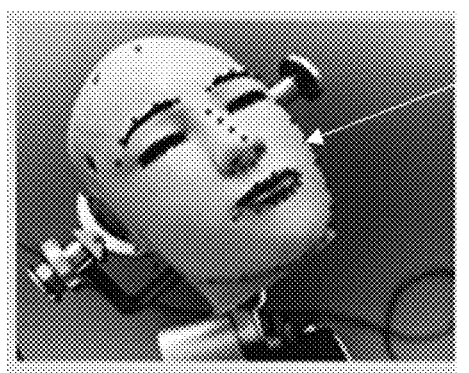
Figure 16H:
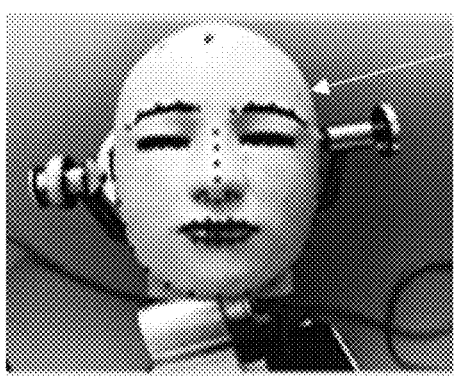

FIG. 11 is a flowchart illustrating an exemplary process for determining a first target posture according to some embodiments of the present disclosure;

FIG. 12 is a flowchart illustrating an exemplary process for adjusting a posture of an image capturing apparatus according to some embodiments of the present disclosure;

FIG. 13A is a front view of an exemplary standard facial model according to some embodiments of the present disclosure;

FIG. 13B is a side view of an exemplary standard facial model according to some embodiments of the present disclosure;

FIG. 14 is a schematic diagram illustrating exemplary facial contour points according to some embodiments of the present disclosure;

FIGS. 15A to 15C are schematic diagrams illustrating an exemplary process for adjusting a posture of an image capturing apparatus according to some embodiments of the present disclosure;

FIG. 16A is a schematic diagram illustrating an image capturing apparatus before posture adjustment according to some embodiments of the present disclosure;

FIG. 16B is a schematic diagram illustrating an image capturing apparatus after posture adjustment according to some embodiments of the present disclosure;

FIGS. 16C, 16E, and 16G are schematic diagrams illustrating image data captured by an image capturing apparatus before posture adjustment according to some embodiments of the present disclosure;

FIGS. 16D, 16F, and 16H are schematic diagrams illustrating image data captured by an image capturing apparatus after posture adjustment according to some embodiments of the present disclosure.

Figure 17:
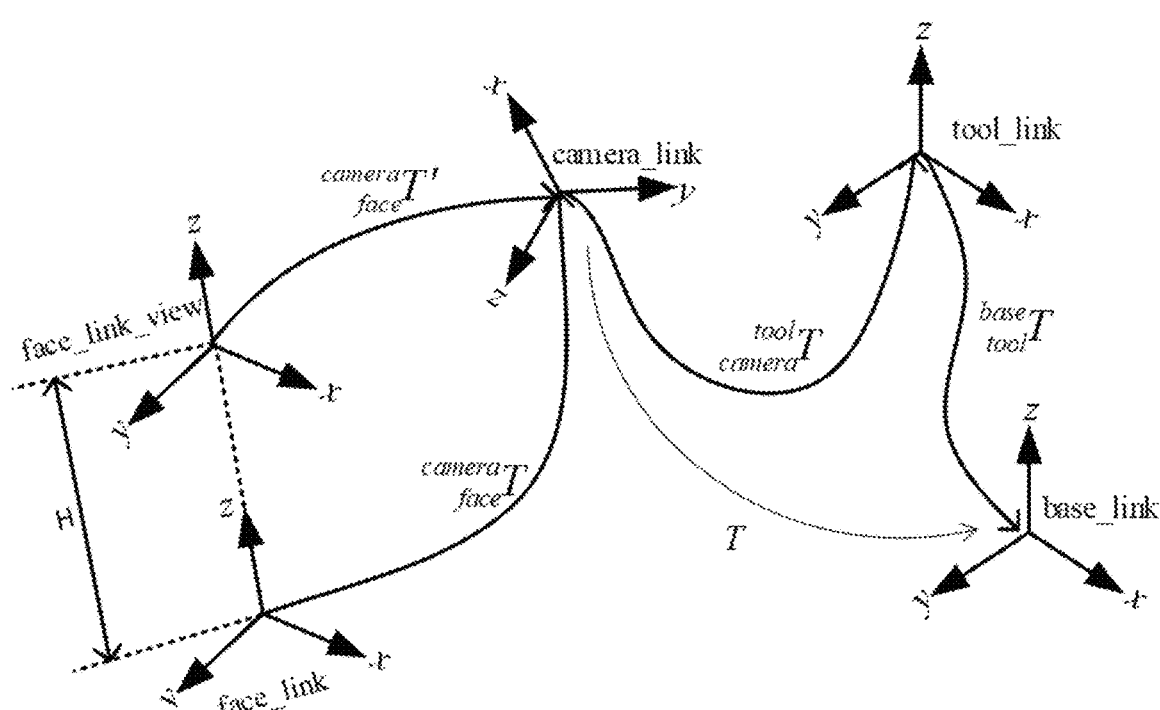
Figure 18:
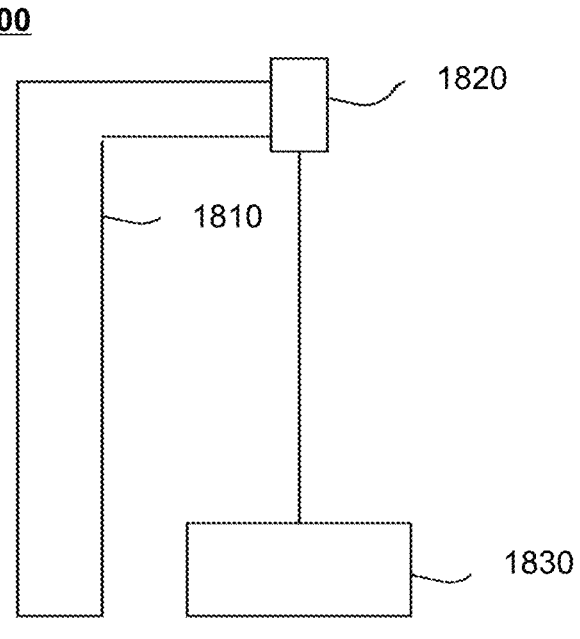
Figure 19:
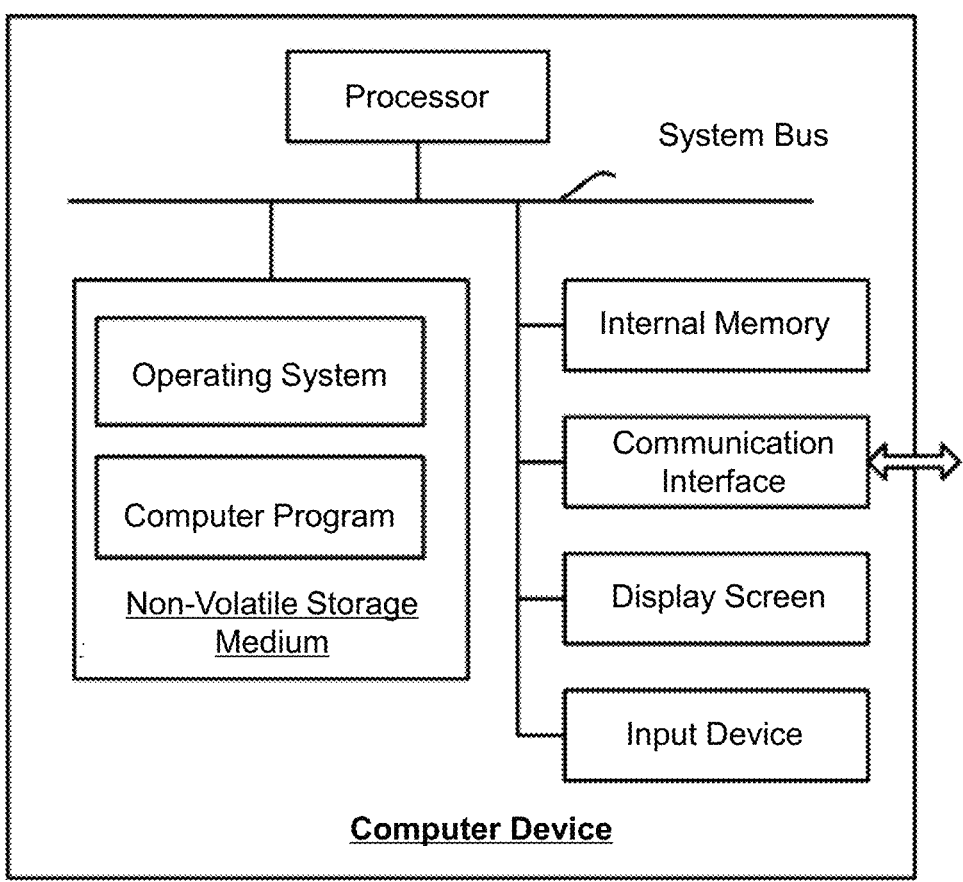

FIG. 17 is a schematic diagram illustrating an exemplary posture adjustment process of an image capturing apparatus according to some embodiments of the present disclosure;

FIG. 18 is a schematic diagram illustrating an exemplary robotic control system according to some embodiments of the present disclosure;

FIG. 19 is a schematic diagram illustrating an exemplary computer device according to some embodiments of the present disclosure; and FIG. 20 is a flowchart illustrating an exemplary robotic control process according to some embodiments of the present disclosure.

DETAILED DESCRIPTION

In order to more clearly illustrate the technical solutions of the embodiments of the present disclosure, the accompanying drawings to be used in the description of the embodiments will be briefly described below. Obviously, the accompanying drawings in the following description are only some examples or embodiments of the present disclosure, and that the present disclosure may be applied to other similar scenarios in accordance with these drawings without creative labor for those of ordinary skill in the art. Unless obviously obtained from the context or the context illustrates otherwise, the same numeral in the drawings refers to the same structure or operation.

It should be understood that "system," "device," "unit," and/or "module" as used herein is a way to distinguish between different components, elements, parts, sections, or assemblies at different levels. However, these words may be replaced by other expressions if other words accomplish the same purpose.

As indicated in the present disclosure and in the claims, unless the context clearly suggests an exception, the words "one," "a," "a kind of," and/or "the" do not refer specifically to the singular but may also include the plural. In general, the terms "including" and "comprising" suggest only the inclusion of clearly identified steps and elements, which do not constitute an exclusive list, and the method or device may also include other steps or elements.

The present disclosure uses flowcharts to illustrate the operations performed by the system according to some embodiments of the present disclosure. It should be understood that the operations described herein are not necessarily executed in a specific order. Instead, they may be executed in reverse order or simultaneously. Additionally, other operations may be added to these processes or certain steps may be removed.

Figure 1A:
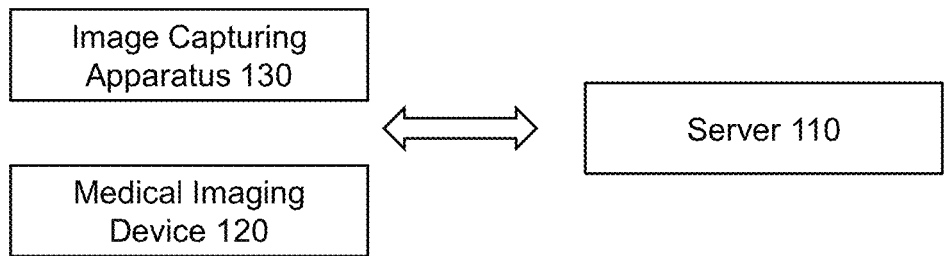
FIG. 1A is a schematic diagram illustrating an exemplary application scenario of a robotic control system according to some embodiments of the present disclosure.

FIG. 1A is a schematic diagram illustrating an application scenario of an exemplary robotic control system 100 according to some embodiments of the present disclosure.

The robotic control system 100 may be used for positioning a robot and adjusting a posture of the robot. As shown in FIG. 1A, in some embodiments, the robotic control system 100 may include a server 110, a medical imaging device 120, and an image capturing apparatus 130. The plurality of components of the robotic control system 100 may be connected to each other via a network. For example, the server 110 and the medical imaging device 120 may be connected or in a communication through a network. As another example, the server 110 and the image capturing apparatus 130 may be connected or in a communication through a network. In some embodiments, connections between the plurality of components of the robotic control system 100 may be variable. For example, the medical imaging device 120 may be directly connected to the image capturing apparatus 130.

The server 110 may be configured to process data or information received from at least one component (e.g., the medical imaging device 120, the image capturing apparatus 130) of the robotic control system 100 or an external data source (e.g., a cloud data center). For example, the server 110 may obtain a first image captured by the image capturing apparatus 130 and a second image captured by the medical imaging device 120, and determine the positioning information of the robot based on the first image and the second image. As another example, the server 110 may capture a target image of a target object using the image capturing apparatus 130, and determine a first target posture of the image capturing apparatus 130 in a base coordinate system. In some embodiments, the server 110 may be a single server or a server group. The server group may be centralized or distributed (e.g., the server 110 may be a distributed system). In some embodiments, the server 110 may be local or remote. In some embodiments, the server 110 may be implemented on a cloud platform or provided virtually. Merely by way of example, the cloud platform may include a private cloud, a public cloud, a hybrid cloud, a community cloud, a distributed cloud, an internal cloud, a multi-tiered cloud, or any combination thereof.

In some embodiments, the server 110 may include one or more components. As shown in FIG. 1C, the server 110 may include one or more (only one shown in FIG. 1C) processors 102, storages 104, transmission devices 106, and input/output devices 108. It is understood by those skilled in the art that the structure shown in FIG. 1C is merely for purposes of illustration, and does not limit the structure of the server 110. For example, the server 110 may include more or fewer components than those shown in FIG. 1C, or may have a configuration different from that shown in FIG. 1C.

The processor 102 may process data or information obtained from other devices or components of the system. The processor 102 may execute program instructions based on the data, the information, and/or processing results, to perform one or more functions described in the present disclosure. In some embodiments, the processor 102 may include one or more sub-processing devices (e.g., a single-core processing device or a multi-core multi-processor device). Merely by way of example, the processor 102 may include a microprocessor unit (MPU), a central processing unit (CPU), an application-specific integrated circuit (ASIC), an application-specific instruction processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction set computer (RISC), or the like, or any combination thereof. In some embodiments, the processor 102 may be integrated or included in one or more other components (e.g., the medical imaging device 120, the image capturing apparatus 130, or other possible components) of the robotic control system 100.

The storage 104 may store data, instructions, and/or other information. For example, the storage 104 may be configured to store a computer program such as a software program and module for an application, for example, a computer program corresponding to positioning methods and posture adjustment methods in the embodiment. The processor 102 may perform various functional applications and data processing by executing the computer program stored in the storage 104, thereby implementing the methods described above. The storage 104 may include high-speed random-access memory and may further include non-volatile memory, such as one or more magnetic storage devices, flash memory, or other non-volatile solid-state storage. In some embodiments, the storage 104 may also include a remote storage configured relative to the processor 102. The remote storage may be connected to a terminal via a network. Examples of the network may include the Internet, intranets, local area networks, mobile communication networks, or any combination thereof. In some embodiments, the storage 104 may be implemented on a cloud platform.

The communication device 106 may be configured to implement communication functions. For example, the communication device 106 may be configured to receive or transmit data via a network. In some embodiments, the communication device 106 may include a network interface controller (NIC) that can communicate with other network devices via a base station to communicate with the Internet. In some embodiments, the communication device 106 may be a radio frequency (RF) module for wireless communication with the Internet.

The input/output device 108 may be configured to input or output signals, data, or information. In some embodiments, the input/output device 108 may facilitate communication between a user and the robotic control system 100. Exemplary input devices may include a keyboard, a mouse, a touch screen, a microphone, or the like, or any combination thereof. Exemplary output devices may include a display device, a speaker, a printer, a projector, or the like, or any combination thereof. Exemplary display devices may include a liquid crystal display (LCD), a light emitting diode (LED) display, a flat panel display, a curved display, a television, a cathode ray tube (CRT), or the like, or any combination thereof.

In some embodiments, the server 110 may be disposed at any location (e.g., a room where the robot is located, a room used for placing the server 110, etc.), as long as the location ensures that the server 110 is in a normal communication with the medical imaging device 120 and the image capturing apparatus 130.

The medical imaging device 120 may be configured to scan the target object in a detection region or a scanning region to obtain imaging data of the target object. In some embodiments, the target object may include a biological and/or a non-biological object. For example, the target object may be an organic and/or inorganic substance with or without life.

In some embodiments, the medical imaging device 120 may be a non-invasive imaging device for diagnostic or research purposes. For example, the medical imaging device 120 may include a single-model scanner and/or a multi-model scanner. The single-model scanner may include, for example, an ultrasound scanner, an X-ray scanner, a computed tomography (CT) scanner, a magnetic resonance imaging (MRI) scanner, an ultrasound examiner, a positron emission tomography (PET) scanner, an optical coherence tomography (OCT) scanner, an ultrasound (US) scanner, an intravascular ultrasound (IVUS) scanner, a near-infrared spectroscopy (NIRS) scanner, a far-infrared (FIR) scanner, or the like, or any combination thereof. The multi-model scanner may include, for example, an X-ray imaging-magnetic resonance imaging (X-ray-MRI) scanner, a positron emission tomography-X-ray imaging (PET-X-ray) scanner, a single-photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, or the like, or any combination thereof. The scanners are merely for purposes of illustration, and do not limit the scope of the present disclosure. Merely by way of example, the medical imaging device 120 may include a CT scanner.

The image capturing apparatus 130 may be configured to capture image data (e.g., the first image, the target image) of the target object. Exemplary image capturing apparatus may include a camera, an optical sensor, a radar sensor, a structured light scanner, or the like, or any combination thereof. For example, the image capturing apparatus 130 may include a device capable of capturing optical data of the target object, such as, the camera (e.g., a depth camera, a stereo triangulation camera, etc.), the optical sensor (e.g., a red-green-blue-depth (RGB-D) sensor, etc.), etc. As another example, the image capturing apparatus 130 may include a device capable of capturing point cloud data of the target object, such as, a laser imaging device (e.g., a time-of-flight (TOF) laser capture device, a point laser capture device, etc.), etc. The point cloud data may include a plurality of data points, wherein each of the plurality of data points may represent a physical point on a body surface of the target object, and one or more feature values (e.g., feature values related to a position and/or a composition) of the physical point may be used to describe the target object. The point cloud data may be used to reconstruct an image of the target object. As still another example, the image capturing apparatus 130 may include a device capable of obtaining location data and/or depth data of the target object, such as, a structured light scanner, a TOF device, a light triangulation device, a stereo matching device, or the like, or any combination thereof. The location data and/or the depth data obtained by the image capturing apparatus 130 may be used to reconstruct the image of the target object.

In some embodiments, the image capturing apparatus 130 may be installed on the robot in a detachable or non-detachable connection manner. For example, the image capturing apparatus 130 may be detachably disposed to an end terminal of a robotic arm of the robot. In some embodiments, the image capturing apparatus 130 may be installed at a location outside the robot using a detachable or non-detachable connection manner. For example, the image capturing apparatus 130 may be disposed at a fixed location in the room where the robot is located.

In some embodiments, a corresponding relationship between the image capturing apparatus 130 and the robot may be determined based on a position of the image capturing apparatus 130, a position of the robot, and a calibration parameter (e.g., a size, a capturing angle) of the image capturing apparatus 130. For example, a mapping relationship (i.e., a first transformation relationship) between a first coordinate system corresponding to the image capturing apparatus 130 and a second coordinate system corresponding to the robot may be determined.

It should be noted that the descriptions are provided for the purposes of illustration, and are not intended to limit the scope of the present disclosure. For persons having ordinary skills in the art, various variations and modifications may be conducted under the teaching of the present disclosure. The features, structures, methods, and other features of the exemplary embodiments described in the present disclosure can be combined in various manners to obtain additional and/or alternative exemplary embodiments. For example, the image capturing apparatus 130 may include a plurality of image capturing apparatus.

Figure 1B:
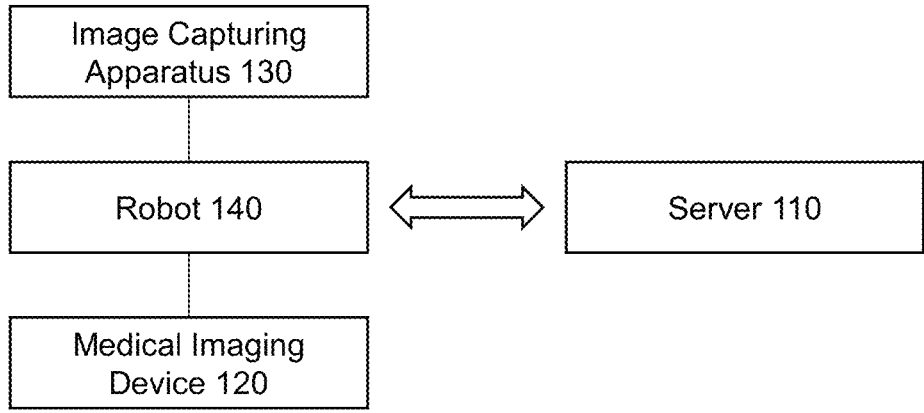
FIG. 1B is a schematic diagram illustrating another exemplary application scenario of the robotic control system according to some embodiments of the present disclosure.
Figure 1C:
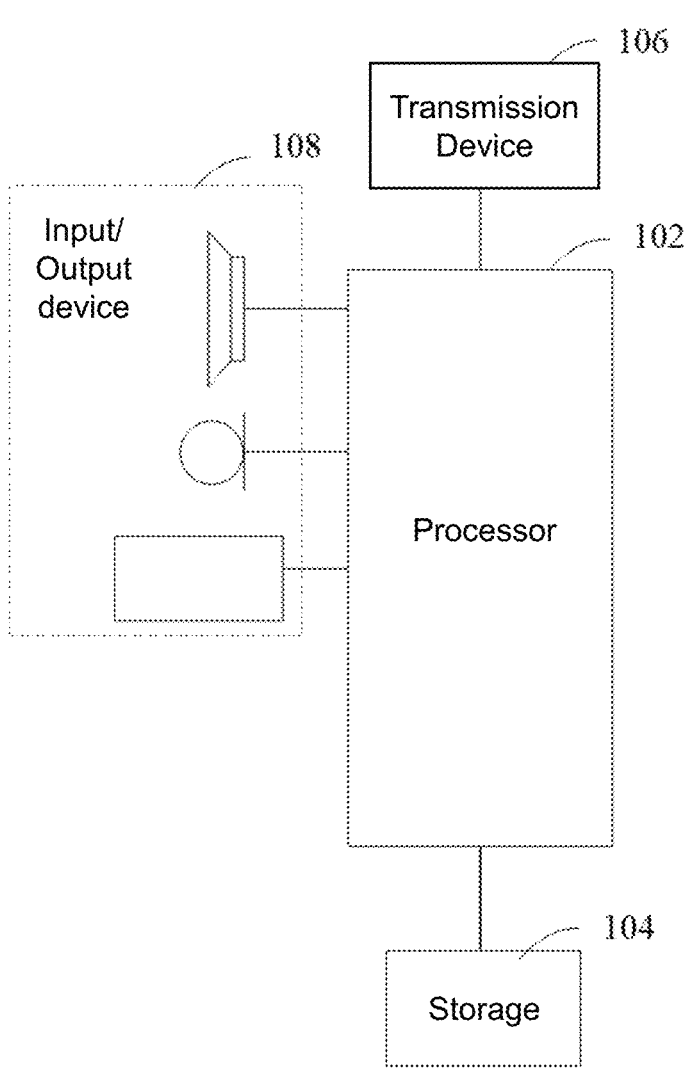
FIG. 1C is a schematic diagram illustrating an exemplary server according to some embodiments of the present disclosure.

In some embodiments, as shown in FIG. 1B, the robot control system 100 may also include a robot 140.

The robot 140 may perform a corresponding operation based on an instruction. For example, the robot 140 may perform a movement operation (e.g., translation, rotation, etc.) based on a movement instruction. Exemplary robots may include a surgical robot, a rehabilitation robot, a bio-robot, a remote rendering robot, a follow-along robot, a disinfection robot, or the like, or any combination thereof.

Merely by way of example, the robot 140 may include a multi-degree-of-freedom robotic arm. The multi-degree-of-freedom robotic arm may include a base joint where a base of the robotic arm is located and an end joint where a flange of the robotic arm is located. The flange of the robotic arm is fixedly connected with end tools, such as surgical tools (e.g., electrode needles, puncture needles, syringes, ablation needles, etc.).

Figure 2:
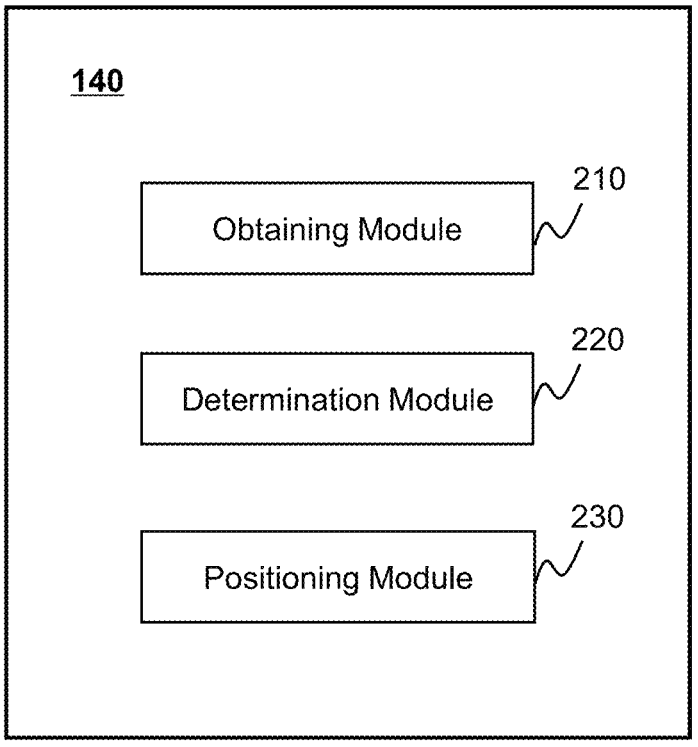
FIG. 2 is a block diagram illustrating an exemplary processor according to some embodiments of the present disclosure.

FIG. 2 is a block diagram illustrating an exemplary processor 102 according to some embodiments of the present disclosure. The processor 102 may include an obtaining module 210, a determination module 220, and a positioning module 230.

The obtaining module 210 may be configured to obtain a first image and a second image of a target object. The first image may be captured using an image capturing apparatus, and the second image may be captured using a medical imaging device. More descriptions regarding the obtaining the first image and the second image may be found in elsewhere in the present disclosure. See, e.g., operation 302 in FIG. 3 and relevant descriptions thereof.

The determination module 220 may be configured to determine at least one target region corresponding to at least one target portion of the target object from the first image.

The at least one target portion may be less affected by physiological motions than other portions. More descriptions regarding the determination of the at least one target region may be found in elsewhere in the present disclosure. See, e.g., operation 304 in FIG. 3 and relevant descriptions thereof.

The positioning module 230 may be configured to determine positioning information of a robot based on the at least one target region and the second image. The positioning information refers to location information of the robot or a specific component (e.g., an end terminal of a robotic arm for mounting a surgical instrument) thereof. In some embodiments, the positioning module 230 may obtain a first transformation relationship between a first coordinate system corresponding to the image capturing apparatus and a second coordinate system corresponding to the robot. The positioning module 230 may further determine a second transformation relationship between the first coordinate system and a third coordinate system corresponding to the medical imaging device based on a registration relationship between the at least one target region and the second image. The positioning module 230 may determine the positioning information of the robot based on the first transformation relationship and the second transformation relationship. More descriptions regarding the determination of the positioning information of the robot may be found in elsewhere in the present disclosure. See, e.g., operation 306 in FIG. 3 and relevant descriptions thereof.

All or some of the modules of the robot control system described above may be implemented through a software, a hardware, or a combination thereof. These modules may be hardware components embedded in or separated from the processor of a computing device, or may be stored in a storage of a computing device in software form, so as to be retrieved by the processor to perform the operations corresponding to each module.

It should be noted that the descriptions of the robot control system and the modules thereof are provided for convenience of illustration, and are not intended to limit the scope of the present disclosure. It should be understood that those skilled in the art, having an understanding of the principles of the system, may arbitrarily combine the various modules or constitute subsystems connected to other modules without departing from the principles. For example, the obtaining module 210, the determination module 220, and the positioning module 230 disclosed in FIG. 2 may be different modules in the same system, or may be a single module that performs the functions of the modules mentioned above. As another example, modules of the robot control system may share a storage module, or each module may have an own storage module. Such modifications may not depart from the scope of the present disclosure.

Figure 3:
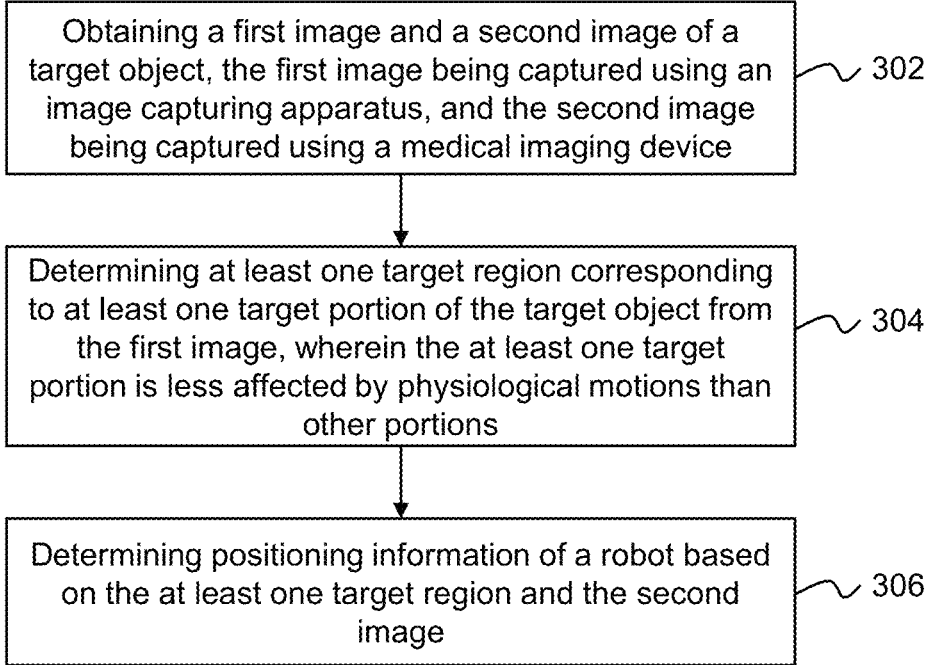
FIG. 3 is a flowchart illustrating an exemplary process for robot positioning according to some embodiments of the present disclosure.

FIG. 3 is a flowchart illustrating an exemplary process 300 for robot positioning according to some embodiments of the present disclosure. In some embodiments, the process 300 may be implemented by the robot control system 100. For example, the process 300 may be stored in a storage device (e.g., the storage 104) in the form of an instruction set (e.g., an application). In some embodiments, the processor 102 (e.g., the one or more modules as shown in FIG. 2) may execute the instruction set and direct one or more components of the robot control system 100 to perform the process 300.

Robots are widely used in the medical field. To accurately control operations of the robots, it is necessary to position the robots. A marker-based positioning technique is commonly used to position robots. Taking neurosurgery as an example, markers need to be implanted in the skull of a patient or attached to the head of the patient, and medical scans are performed on the patient with the markers. Furthermore, corresponding position information of the markers in an image space and a physical space may be determined, thereby positioning the robot based on a corresponding relationship between the image space and the physical space. However, the markers usually cause additional harm to the patient. In addition, once there is a relative displacement between the markers and the head of the patient in the preoperative images, the accuracy of the robot positioning is reduced, thereby affecting preoperative planning or surgical operations. Therefore, it is necessary to provide an effective system and method for robot positioning. In some embodiments, the robot may be positioned by performing the following operations in the process 300.

In 302, the processor 102 (e.g., the obtaining module 210) may obtain a first image and a second image of a target object. The first image may be obtained using an image capturing apparatus, and the second image may be obtained using a medical imaging device.

In some embodiments, the target object may include a biological object and/or a non-biological object. For example, the target object may be an organic and/or inorganic substance with or without life. As another example, the target object may include a specific part, organ, and/or tissue of a patient. Merely by way of example, in a scenario of neurosurgery, the target object may be the head or face of the patient.

The first image refers to an image obtained using the image capturing apparatus (e.g., the image capturing apparatus 130). The first image may include a three-dimensional (3D) image and/or a two-dimensional (2D) image. In some embodiments, the first image may include a depth image of the target object, which includes distance information from points on the surface of the target object to a reference point.

In some embodiments, the processor 102 may obtain image data of the target object from the image capturing apparatus (e.g., the image capturing apparatus 130), and determine the first image of the target object based on the image data. For example, when the image capturing apparatus is a camera, the processor 102 may obtain optical data of the target object from the camera, and determine the first image based on the optical data. As another example, when the image capturing apparatus is a laser imaging device, the processor 102 may obtain point cloud data of the target object from the laser imaging device, and determine the first image based on the point cloud data. As still another example, when the image capturing apparatus is a depth camera, the processor 102 may obtain depth data of the target object from the depth camera, and generate a depth image based on the depth data as the first image. In some embodiments, the processor 102 may directly obtain the first image from the image capturing apparatus or a storage device (e.g., the storage 104).

In some embodiments, before the first image of the target object is captured using the image capturing apparatus, a surgical position of the target object may be determined based on preoperative planning. The target object may be fixed, and a posture of the image capturing apparatus may be adjusted such that the image capturing apparatus captures the target object from a target shooting angle and/or a target shooting height. For example, the posture of the image capturing apparatus may be adjusted such that the face of a patient is completely within a field of view of the image capturing apparatus, and the image capturing apparatus is aligned vertically with the face of the patient for imaging.

More descriptions regarding the adjustment of the posture of the image capturing apparatus may be found in elsewhere in the present disclosure. See, e.g., FIGS. 9-17 and relevant descriptions thereof.

The second image refers to a medical image captured using a medical imaging device (e.g., the medical imaging device 120). Merely by way of example, the medical imaging device may be a CT device. Correspondingly, the processor 102 may obtain CT image data of the target object using the CT device, and reconstruct a CT image based on the CT image data. The processor 102 may further obtain the second image by performing a 3D reconstruction on the CT image.

In some embodiments, the processor 102 may directly obtain the second image of the target object from the medical imaging device (e.g., the medical imaging device 120). Alternatively, the processor 102 may obtain the second image of the target object from a storage device (e.g., the storage 104) that stores the second image of the target object.

In some embodiments, the processor 102 may first obtain a first initial image and/or a second initial image, wherein the first initial image is captured using the image capturing apparatus, and the second initial image is captured using the medical imaging device. The processor 102 may generate the first image and/or the second image by processing the first initial image and/or the second initial image. Merely by way of example, the processor 102 may obtain a full-body depth image and a full-body CT image of a patient. The processor 102 may obtain the first image by segmenting a portion corresponding to the face of the patient from the full-body depth image. The processor 102 may obtain a 3D reconstructed image by performing a 3D reconstruction on the full-body CT image, and obtain the second image by segmenting a portion corresponding to the face of the patient from the 3D reconstructed image.

In some embodiments, after the first image and the second image of the target object are obtained, the processor 102 may perform a preprocessing operation (e.g., target region segmentation, dimension adjustment, image resampling, image normalization, etc.) on the first image and the second image. The processor 102 may further perform other operations of the process 300 on the preprocessed first image and the preprocessed second image. For purposes of illustration, the first image and the second image are taken as examples for describing the execution process of the process 300.

In 304, the processor 102 (e.g., the determination module 220) may determine at least one target region corresponding to at least one target portion of the target object from the first image.

In some embodiments, the at least one target portion may be less affected by physiological motions than other portions. The physiological motions may include blinking, respiratory motions, cardiac motions, etc. Merely by way of example, the at least one target portion may be a static facial region. The static facial region refers to a region that is less affected by changes in facial expressions, such as, a region near a facial bone structure. In some embodiments, the processor 102 may capture shape data of human faces under different facial expressions, obtain a region that is less affected by the changes in facial expressions by performing a statistical analysis on the shape data, and determine the region as the static facial region. In some embodiments, the processor 102 may determine the static facial region using physiological structure information. For example, the processor 102 may determine a region close to the facial bone structure as the static facial region. Exemplary static facial regions may include a forehead region, a nasal bridge region, etc.

A target region refers to a region corresponding to a target portion of the target object from the first image. In some embodiments, the processor 102 may determine the at least one target region corresponding to the at least one target portion of the target object from the first image using an image recognition technique (e.g., a 3D image recognition model). Merely by way of example, the processor 102 may input the first image into the 3D image recognition model, and the 3D image recognition model may segment the at least one target region from the first image. The 3D image recognition model may be obtained by training, based on a plurality of training samples, an initial model. Each of the plurality of training samples may include a sample first image of a sample object and a corresponding sample target region, wherein the sample first image is determined as a training input, and the corresponding sample target region is determined as a training label. In some embodiments, the processor 102 (or other processing devices) may iteratively update the initial model based on the plurality of training samples until a specific condition is met (e.g., a loss function is less than a certain threshold, a certain count of training iterations is performed).

In some embodiments, the first image may be a 3D image (e.g., a 3D depth image). The processor 102 may obtain a 2D reference image of the target object captured using the image capturing apparatus. The processor 102 may determine at least one reference region corresponding to the at least one target portion based on the 2D reference image. Further, the processor 102 may determine the at least one target region from the first image based on the at least one reference region. More descriptions regarding the determination of the at least one target region may be found in elsewhere in the present disclosure. See, e.g., FIG. 4 and relevant descriptions thereof.

In 306, the processor 102 (e.g., the positioning module 230) may determine positioning information of a robot based on the at least one target region and the second image.

The positioning information of the robot refers to location information of the robot or a specific component (e.g., an end terminal of a robotic arm for mounting a surgical instrument) thereof. For convenience of illustration, the positioning information of the specific component of the robot is referred to as the positioning information of the robot later in the present disclosure. In some embodiments, the positioning information of the robot may include a positional relationship between the robot and a reference object (e.g., the target object, a reference object determined by a user and/or the system), a transformation relationship between a coordinate system corresponding to the robot (i.e., a second coordinate system) and other coordinate systems (e.g., a first coordinate system, a third coordinate system), etc. For example, the positioning information may include a positional relationship between coordinates of the robot and coordinates of the target object in a same coordinate system.

In some embodiments, the processor 102 may obtain a first transformation relationship between the first coordinate system corresponding to the image capturing apparatus and the second coordinate system corresponding to the robot. The processor 102 may further determine a second transformation relationship between the first coordinate system and the third coordinate system corresponding to the medical imaging device based on a registration relationship between the at least one target region and the second image.

The processor 102 may then determine the positioning information of the robot based on the first transformation relationship and the second transformation relationship. For example, the processor 102 may determine a third transformation relationship between the second coordinate system corresponding to the robot and the third coordinate system corresponding to the medical imaging device based on the first transformation relationship and the second transformation relationship.

The first coordinate system corresponding to the image capturing apparatus refers to a coordinate system established based on the image capturing apparatus, for example, a 3D coordinate system established with a geometric center of the image capturing apparatus as an origin. The second coordinate system corresponding to the robot refers to a coordinate system established based on the robot. For example, the second coordinate system may be a coordinate system of the end terminal of the robotic arm, a coordinate system of a tool of the robot, etc. The third coordinate system corresponding to the medical imaging device refers to a coordinate system established based on the medical imaging device, for example, a 3D coordinate system established with a rotation center of a gantry of the medical imaging device as an origin. As used in the present disclosure, a transformation relationship between two coordinate systems may represent a mapping relationship between positions in the two coordinate systems. For example, the transformation relationship may be represented as a transformation matrix that can transform a first coordinate of a point in one coordinate system to a corresponding second coordinate in another coordinate system. In some embodiments, a transformation relationship between a coordinate system corresponding to a first object and a coordinate system corresponding to a second object may also be referred to as a relative positional relationship or a position mapping relationship between the first object and the second object. For example, the first transformation relationship may also be referred to as a relative positional relationship or a position mapping relationship between the image capturing apparatus and the robot.

In some embodiments, the processor 102 may determine the first transformation relationship using a preset calibration technique (e.g., a hand-eye calibration algorithm). For example, the processor 102 may construct an intermediate reference object, and determine the first transformation relationship based on a first coordinate of the intermediate reference object in the first coordinate system (or a relative positional relationship between the intermediate reference object and the image capturing apparatus) and a second coordinate of the intermediate reference object in the second coordinate system (or a relative positional relationship between the intermediate reference object and the robot). The image capturing apparatus may be installed on the robot, for example, at the end terminal of a manipulator arm of the robot. Alternatively, the image capturing apparatus may be disposed at any fixed location in a room where the robot is located, and the processor 102 may determine a mapping relationship between a position of the robot and a position of the image capturing apparatus based on the position of the image capturing apparatus, the position of the robot, and a position of the intermediate reference object.

In some embodiments, the processor 102 may determine the second transformation relationship between the first coordinate system corresponding to the image capturing apparatus and the third coordinate system corresponding to the medical imaging device based on the registration relationship between at least one target region and the second image. The registration relationship may reflect a corresponding relationship and/or a coordinate transformation relationship between points in the at least one target region and points in the second image. Since the at least one target region and the second image correspond to the same target object, there may be the corresponding relationship between the points in the at least one target region and the points in the second image, so the registration relationship between the at least one target region and the second image can be determined through a registration technique. More descriptions regarding the determination of the registration relationship between the at least one target region and the second image may be found in elsewhere in the present disclosure. See, e.g., FIG. 5 and relevant descriptions thereof.

According to some embodiments of the present disclosure, the first image and the second image of the target object may be obtained, the at least one target region corresponding to the at least one target portion of the target object may be determined from the first image, and the positioning information of the robot may be determined based on the at least one target region and the second image. The transformation relationships between the coordinate systems of the robot, the image capturing apparatus, and the medical imaging device may be determined through the at least one target region and the second image (i.e., a medical image), and no additional markers need to be attached or disposed on the target object, thereby avoiding additional harm to the target object. Using the at least one target region and the second image for registration, instead of directly using the first image and the second image for registration, the influence of the physiological motions on a registration result can be reduced, thereby improving the accuracy of the registration result. In addition, the robot can be positioned based on the medical image, which can improve the accuracy of the robot positioning, thereby improving the accuracy of preoperative planning or surgical operations.

It should be noted that the above descriptions of the process 300 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the process 300 may be accomplished with one or more additional operations not described, and/or without one or more of the operations discussed. For example, after the positioning information of the robot is determined, the processor 102 may verify the positioning information to ensure the accuracy of the robot positioning. As another example, the processor 102 may control the robot to perform a surgical plan. For instance, the processor 102 may control the robot to move to a target location and perform surgical operations based on the positioning information and the surgical plan.

Figure 4:
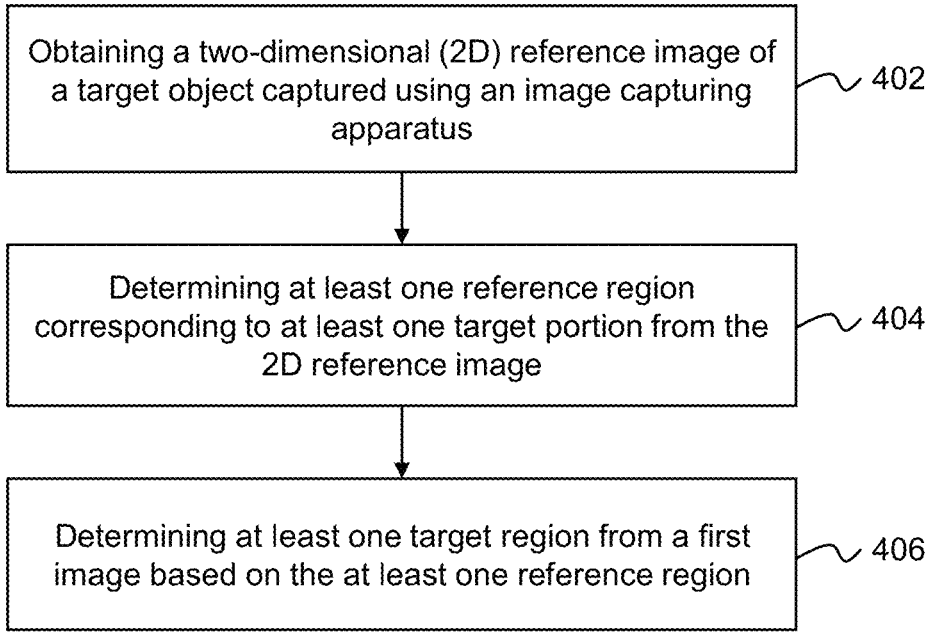
FIG. 4 is a flowchart illustrating an exemplary process for determining at least one target region according to some embodiments of the present disclosure.

FIG. 4 is a flowchart illustrating an exemplary process 400 for determining at least one target region according to some embodiments of the present disclosure. In some embodiments, the process 400 may be implemented by the robot control system 100. For example, the process 400 may be stored in a storage device (e.g., the storage 104) in the form of an instruction set (e.g., an application). In some embodiments, the processor 102 (e.g., the one or more modules as shown in FIG. 2) may execute the instruction set and direct one or more components of the robot control system 100 to perform the process 400. In some embodiments, the at least one target region described in operation 304 of FIG. 3 may be determined according to the process 400.

In 402, the processor 102 (e.g., the determination module 220) may obtain a 2D reference image of a target object captured using an image capturing apparatus.

In some embodiments, the first image described in FIG. 3 may be a 3D image, such as a depth image. The processor 102 may directly obtain the 2D reference image of the target object from the image capturing apparatus or a storage device. For example, the image capturing apparatus may be a depth camera or a laser capturing device, which can simultaneously capture the 2D reference image and the depth image of the target object. In some embodiments, the processor 102 may generate the 2D reference image of the target object based on the first image. For example, the processor 102 may transform the 3D first image into the 2D reference image using an image transformation algorithm.

In 404, the processor 102 (e.g., the determination module 220) may determine at least one reference region corresponding to at least one target portion from the 2D reference image.

Figure 8:
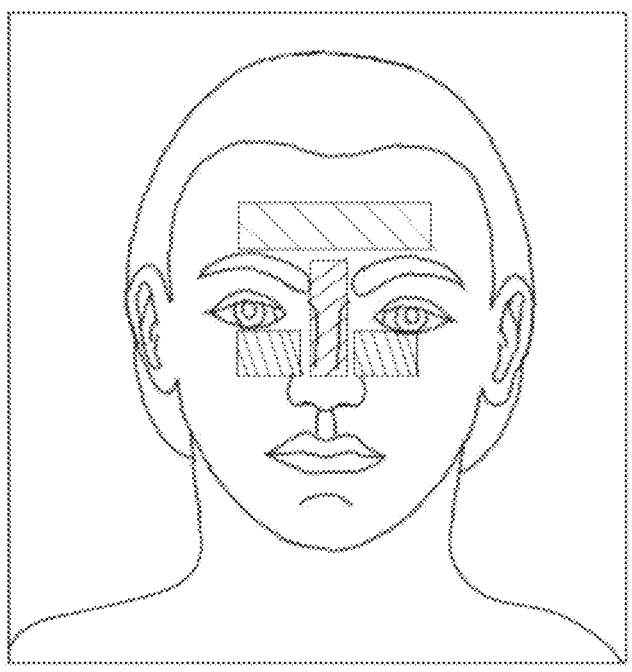
FIG. 8 is a schematic diagram illustrating an exemplary two-dimensional facial image according to some embodiments of the present disclosure.

A reference region refers to a region in the 2D reference image corresponding to a target portion. For example, FIG. 8 is a schematic diagram illustrating an exemplary 2D reference image according to some embodiments of the present disclosure. As shown in FIG. 8, shaded regions may be reference regions corresponding to facial static regions, e.g., the forehead, the bridge of the nose, etc.

In some embodiments, the processor 102 may determine at least one feature point associated with the at least one target portion from the 2D reference image. For example, the processor 102 may determine the at least one feature point associated with the at least one target portion from the 2D reference image based on a preset feature point extraction algorithm. Exemplary feature point extraction algorithms may include a scale-invariant feature transform (SIFT) algorithm, a speeded-up robust features (SURF) algorithm, a histogram of oriented gradient (HOG) algorithm, a difference of gaussian (DOG) algorithm, a feature point extraction algorithm based on a machine learning model, or the like, or any combination thereof.

Figure 7:
FIG. 7 is a schematic diagram illustrating exemplary facial feature points according to some embodiments of the present disclosure.

For example, the processor 102 may perform feature point extraction on the 2D reference image using an image feature point extraction model (e.g., a pre-trained neural network model). The processor 102 may input the 2D reference image into the image feature point extraction model, and the image feature point extraction model may output the at least one feature point associated with the at least one target portion in the 2D reference image. Merely by way of example, the 2D reference image may be a 2D facial image. The at least one feature point in the 2D facial image associated with the at least one target portion may be obtained by inputting the 2D facial image into the image feature point extraction model (e.g., a face feature point detection model). As shown in FIG. 7, facial feature points identified from the 2D facial image may include feature points of the eyes, the mouth, the eyebrows, the nose, etc.

Further, the processor 102 may determine the at least one reference region corresponding to the at least one target portion based on the at least one feature point. For example, a region of the eyes may be determined based on the feature points of the eyes. In some embodiments, each of the at least one feature point may have a fixed sequence number, and the at least one reference region may be determined from the 2D reference image based on the fixed sequence number of the feature point. For example, referring to FIG. 7 again, feature points with sequence numbers of 37 to 42 in the facial feature points are feature points corresponding to a right eye, and a right eye region may be determined based on the feature points.

In some embodiments, the processor 102 may determine the at least one reference region corresponding to the at least one target portion from the 2D reference image through an image identification technique (e.g., a 2D image identification model). Merely by way of example, the processor 102 may input the 2D reference image into the 2D image identification model, and the 2D image identification model may segment the at least one reference region from the 2D reference image. The 2D image identification model may be obtained by training based on training samples. Each of the training samples may include a sample 2D reference image of a sample object and a corresponding sample reference region. The sample 2D reference image may be a training input, and the corresponding sample reference region may be a training label. In some embodiments, the processor 102 (or other processing devices) may iteratively update an initial model based on the training samples until a specific condition is met (e.g., a loss function is less than a certain threshold, a count of training iterations reaches a certain count, etc.).

In 406, the processor 102 (e.g., the determination module 220) may determine at least one target region from the first image based on the at least one reference region.

In some embodiments, the processor 102 may determine the at least one target region corresponding to the at least one reference region based on a mapping relationship between the 2D reference image and the first image. The mapping relationship between the 2D reference image and the first image may be determined based on parameter(s) of the image capturing apparatus.

According to some embodiments of the present disclosure, the at least one target region corresponding to the at least one target portion of the target object may be determined based on the at least one reference region corresponding to the at least one target portion determined from the 2D reference image. Compared to directly determining the at least one target region from the first image, by determining the at least one target region based on the 2D reference image, an impact of a depth parameter in the first image on the determination of the at least one target region can be reduced, thereby improving the accuracy of the target region determination. In addition, during the determination process, only one 2D reference image and one first image are processed, which can reduce the data volume during the determination process, thereby saving time and resources for data processing.

It should be noted that the above descriptions of the process 400 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the process 400 may be accomplished with one or more additional operations not described, and/or without one or more of the operations discussed. For example, the at least one target region may be determined using a plurality of 2D reference images and the first image. As another example, at least one corresponding feature point may be determined from the first image based on the at least one feature point, and then the at least one target region may be determined based on the at least one corresponding feature point.

Figure 5:
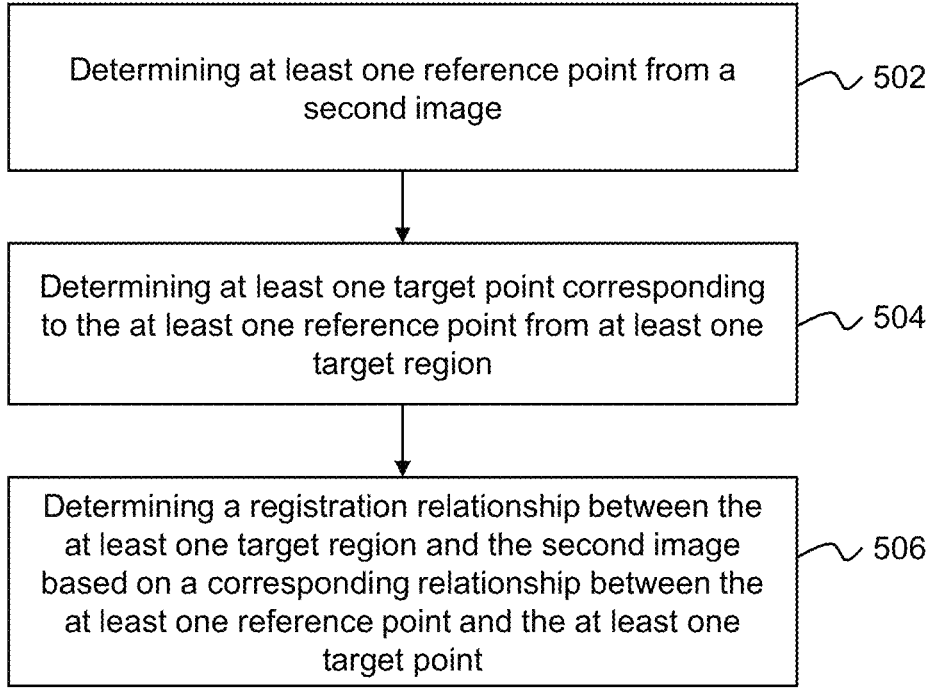
FIG. 5 is a flowchart illustrating an exemplary process for determining a registration relationship according to some embodiments of the present disclosure.

FIG. 5 is a flowchart illustrating an exemplary process 500 for determining a registration relationship according to some embodiments of the present disclosure. In some embodiments, the process 500 may be implemented by the robot control system 100. For example, the process 500 may be stored in a storage device (e.g., the storage 104) in the form of an instruction set (e.g., an application). In some embodiments, the processor 102 (e.g., the one or more modules as shown in FIG. 2) may execute the instruction set and direct one or more components of the robot control system 100 to perform the process 500. In some embodiments, the registration relationship described in operation 306 of FIG. 3 may be determined according to the process 500.

In some embodiments, a registration relationship between at least one target region and a second image may be determined through a registration technique. Exemplary registration techniques may include a global registration technique, a local registration technique, etc. The global registration technique may be used for registration based on a corresponding relationship between a target plane in the at least one target region and a reference plane in the second image. The local registration may be used for registration based on a corresponding relationship between target points in the at least one target region and reference points in the second image. Merely by way of example, the registration relationship between the at least one target region and the second image may be determined through the global registration technique and/or the local registration technique.

In 502, the processor 102 (e.g., the positioning module 230) may determine at least one reference point from the second image.

In some embodiments, the at least one reference point may form at least one reference point set, and each of the at least one reference point set may include at least three reference points located on a same plane. In other words, each reference point set (e.g., the at least three reference points) may determine a reference plane from the second image. Operation 502 is used to determine at least one reference plane from the second image. In some embodiments, a count of reference points in each reference point set may be determined based on actual condition(s). For example, each reference point set may include at least four reference points located on a same plane. It should be noted that three points are sufficient to define a plane, but using a reference point set including at least four reference points can improve the accuracy of the determination of a positional relationship of reference points in the reference plane in a medical image, thereby improving the accuracy of the determination of the registration relationship.

In some embodiments, the processor 102 may randomly determine the at least one reference point from the second image, and determine position information of the at least one reference point in a third coordinate system corresponding to a medical imaging device. For example, the processor 102 may determine four reference points located in a same plane from the second image through a random sampling algorithm, and determine corresponding coordinates of the four reference points in the third coordinate system corresponding to the medical imaging device. The four reference points may form a reference point set.

In 504, the processor 102 (e.g., the positioning module 230) may determine at least one target point corresponding to the at least one reference point from the at least one target region.

In some embodiments, the processor 102 may determine the at least one target point corresponding to the at least one reference point in the at least one target region through the global registration technique.

In some embodiments, for each reference point set in the at least one reference point set, the processor 102 may determine positional relationships between reference point pairs among the reference point set. The reference point pairs may include adjacent reference points or non-adjacent reference points. A positional relationship between one reference point pair may include a distance between the reference points in the reference point pair, a relative direction between the reference points in the reference point pair, etc. In some embodiments, the positional relationships between the reference point pairs in a reference point set may be represented through vector information. For example, the processor 102 may determine a distance and a direction between each two reference points in the reference point set based on coordinates of the at least three reference points in the reference point set, and represent the distance and the direction through vector information. In other words, the processor 102 may determine vector information of the reference point set based on the distance and the direction between each two reference points among the reference point set.

In some embodiments, for each reference point set in the at least one reference point set, the processor 102 may determine a target point set corresponding to the reference point set from the at least one target region based on the positional relationships between the reference point pairs in the reference point set. Each target point set may include at least three target points located in a same plane. In other words, the processor 102 may determine a target plane from the at least one target region based on each target point set (e.g., the at least three target points). In some embodiments, the processor 102 may determine the target point set corresponding to the reference point set from the at least one target region based on the vector information of the reference point set. For example, the processor 102 may determine a plurality of candidate target point sets from the at least one target region. A count of candidate target points in each candidate target point set may be the same as a count of reference points in the reference point set. The processor 102 may further determine a candidate target point set that is most similar to the reference point set as the target point set. The most similar to the reference point set refers to that a difference between vector information of a candidate target point set and the vector information of the reference point set is minimum.

Figure 6A:
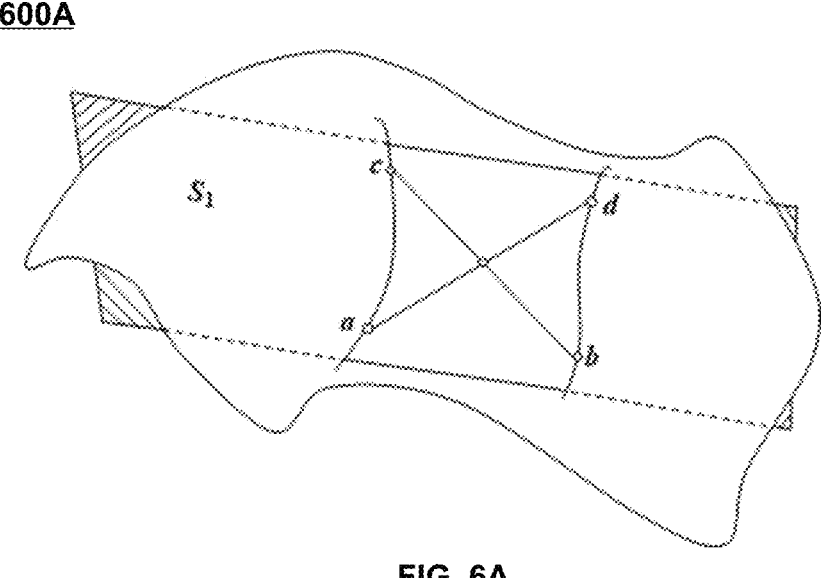
FIG. 6A is a schematic diagram illustrating an exemplary reference point set in a second image according to some embodiments of the present disclosure.
Figure 6B:
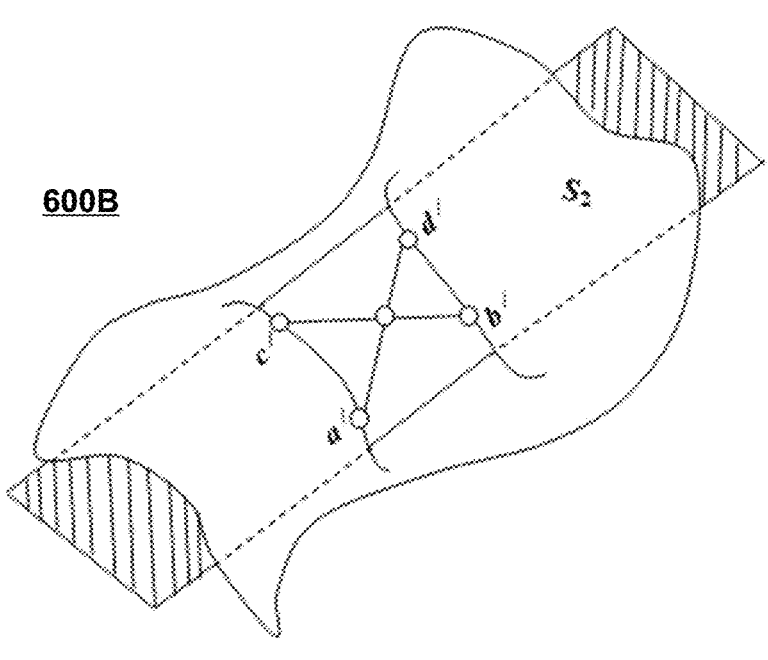
FIG. 6B is a schematic diagram illustrating an exemplary candidate target point set in at least one target region according to some embodiments of the present disclosure.

Merely by way of example, for each reference point set in the at least one reference point set, the processor 102 may determine a first distance between each two reference points among the reference point set based on the vector information of the reference point set, and determining a second distance between each two candidate target points among each of the plurality of candidate target point sets in the at least one target region. The processor 102 may determine a deviation between each first distance and the corresponding second distance. Further, the processor 102 may determine the target point set corresponding to the reference point set from the plurality of candidate target point sets based on the deviation between each first distance and the corresponding second distance. Referring to FIGS. 6A and 6B, FIG. 6A is a schematic diagram illustrating an exemplary reference point set 600A in a second image according to some embodiments of the present disclosure. As shown in FIG. 6A, the reference point set 600A in the second image may include four points (e.g., reference points) a, b, c, and d, and the four points a, b, c, and d may form a plane S1. The processor 102 may determine distances between point pairs a-b, a-c, a-d, b-c, b-d, and c-d as first distances based on position information (e.g., vector information) of the four points a, b, c, and d. FIG. 6B is a schematic diagram illustrating an exemplary candidate target point set 600B in at least one target region according to some embodiments of the present disclosure. As shown in FIG. 6B, the candidate target point set 600B may include four points (e.g., candidate target points) a', b', c', and d', and the four points a', b', c', and d' may form a plane S2. The processor 102 may determine distances between point pairs a'-b', a'-c', a'-d', b'-c', b'-d', and c'-d' as second distances based on position information of the four points a', b', c', and d'.

For each of the first distances, the processor 102 may determine a deviation between the first distance and the corresponding second distance. The deviation may include a difference between the first distance and the second distance or a ratio of the first distance to the second distance. For example, the processor 102 may determine distance differences between point pairs a-b and a'-b', a-c and a'-c', . . . , c-d and c'-d', respectively. As another example, the processor 102 may determine distance ratios of point pairs a-b to a'-b', a-c to a'-c', . . . , c-d to c'-d', respectively. Further, the processor 102 may determine a difference between the candidate target point set and the reference point set based on the deviations between the first distances and the second distances. For example, the processor 102 may determine a sum of the distance differences, and determine the sum as the difference between the candidate target point set and the reference point set. As anther example, the processor 102 may determine an average of the distance differences, and determine the average as the difference between the candidate target point set and the reference point set. In some embodiments, the at least one target region may include a plurality of candidate target point sets. The processor 102 may determine a difference between each of the plurality of candidate target point sets and the reference point set. In some embodiments, the processor 102 may determine a candidate target point set with the minimum difference as the target point set.

The target point set may be determined based on the distance between each reference point pair in the reference point set and the distance between each candidate target point pair in the candidate target point set. Since the position information of each reference point and each candidate target point is known, the determination of the distances can be simple, thereby improving the efficiency of the determination of the target point set corresponding to the reference point set.

In some embodiments, the processor 102 may determine a target point corresponding to each reference point in the reference point set based on the target point set. For example, the processor 102 may determine, based on the target point set, a target point corresponding to each reference point through a positional corresponding relationship between each target point in the target point set and each reference point in the reference point set.

By using the global registration technique, the processor 102 may determine the target point set corresponding to the reference point set in the second image from the at least one target region, thereby determining the target points corresponding to the reference points. The implementation of the global registration technique is simple, which can improve the efficiency of the target point determination, and ensure the accuracy of the target point selection.

In some embodiments, the processor 102 may determine the target points corresponding to the reference points based on the local registration technique, thereby registering the reference points with the target points. For example, the processor 102 may determine the target points corresponding to the reference points through an iterative closest point (ICP) algorithm.

Merely by way of example, the processor 102 may obtain position information (e.g., coordinates, depth information, etc.) for each candidate target point in the at least one target region. The processor 102 may determine the target point corresponding to each reference point based on the position information of each candidate target point, the position information of each reference point, and a preset iterative closest point algorithm. For example, for each reference point, the processor 102 may determine, based on the iterative closest point algorithm, a target point with a closest distance (e.g., a Euclidean distance) to the reference point according to the position information of the reference point in the second image and the position information of each candidate target point in the at least one target region. For instance, the processor 102 may determine a reference point in the second image, search for a closest candidate target point in the at least one target region, and determine the closest candidate target point as the corresponding target point of the reference point. The processor 102 may determine, based on the reference points and the corresponding target points, a transformation matrix (e.g., a rotation matrix and/or a translation matrix) between the at least one target region and the second image. The processor 102 may transform the at least one target region based on the transformation matrix, and determine new target points corresponding to the reference points from at least one transformed target region. The above process may be iterated until a specific condition is met. For example, the specific condition may include that distances between the reference points and corresponding newest target points are less than a preset threshold, a count of iterations reaches a preset threshold, or differences between distances from the reference points to the corresponding newest target points and distances from the reference points to the corresponding previous target points are less than a preset threshold. The processor 102 may determine the registration relationship based on a corresponding relationship (e.g., the transformation matrix) between the reference points and target points in the last iteration.

In some embodiments, the processor 102 may also determine an initial registration relationship between the at least one target region and the second image based on the global registration technique as described above. Further, the processor 102 may determine the registration relationship by adjusting the initial registration relationship using the local registration technique (e.g., the iterative closest point algorithm).

Merely by way of example, the processor 102 may determine the initial registration relationship (i.e., an initial corresponding relationship (e.g., an initial transformation matrix)) between the target points in the at least one target region and the reference points in the second image based on the global registration technique. For each target point, the processor 102 may determine or adjust an initial reference point corresponding to each target point based on the preset iterative closest point algorithm. For example, for each target point, the processor 102 may determine a reference point with a closest distance (e.g., a Euclidean distance) to the target point from the reference points. If the reference point is different from the initial reference point in the initial registration relationship, the initial registration relationship may be updated, and the reference point with the closest distance to the target point may be determined as the corresponding new reference point. The processor 102 may determine, based on the target points and the corresponding new reference points, a transformation matrix (e.g., a rotation matrix and/or a translation matrix) between the at least one target region and the second image. The processor 102 may transform the at least one target region based on the transformation matrix, and determine new reference points from the second image based on transformed target points. The above process may be iterated until a specific condition is met. For example, the specific condition may include that distances between the transformed target points and the new reference points are less than a preset threshold, a count of iterations reaches a preset threshold, or differences between distances from the transformed target points to the new reference points and distances from the last reference points to the last target points are less than a preset threshold. The processor 102 may determine the registration relationship by adjusting the initial registration relationship between the at least one target region and the second image based on a corresponding relationship (e.g., the transformation matrix) between target points and reference points in the last iteration.

According to some embodiments of the present disclosure, the target points can be determined from the at least one target region based on the reference points in the second image, so that the registration relationship is determined based on the position information of the reference points and the target points. By registering with the reference points and the target points, data computation and processing time can be reduced, thereby simplifying the processing procedure. In addition, the registration relationship between the at least one target region and the second image can be determined by simultaneously using the global registration technique and the local registration technique, which improves the accuracy of the determination.

In 506, the processor 102 (e.g., the positioning module 230) may determine the registration relationship between the at least one target region and the second image based on a corresponding relationship between the at least one reference point and the at least one target point.

In some embodiments, the processor 102 may obtain the position information of the at least one reference point and the at least one target point, and determine a transformation relationship between the position information of the at least one reference point and the at least one target point as the registration relationship. For example, the processor 102 may determine a transformation matrix between the at least one reference point and the at least one target point based on coordinates of the at least one reference point and the at least one target point. The transformation matrix may be represented as a transformation relationship between a coordinate system in which the at least one reference point is located and a coordinate system in which the at least one target point reference points is located. Further, the transformation matrix may also represent the registration relationship between the at least one target region and the second image.

It should be noted that the above descriptions of the process 500 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the process 500 may be accomplished with one or more additional operations not described, and/or without one or more of the operations discussed.

Figure 9:
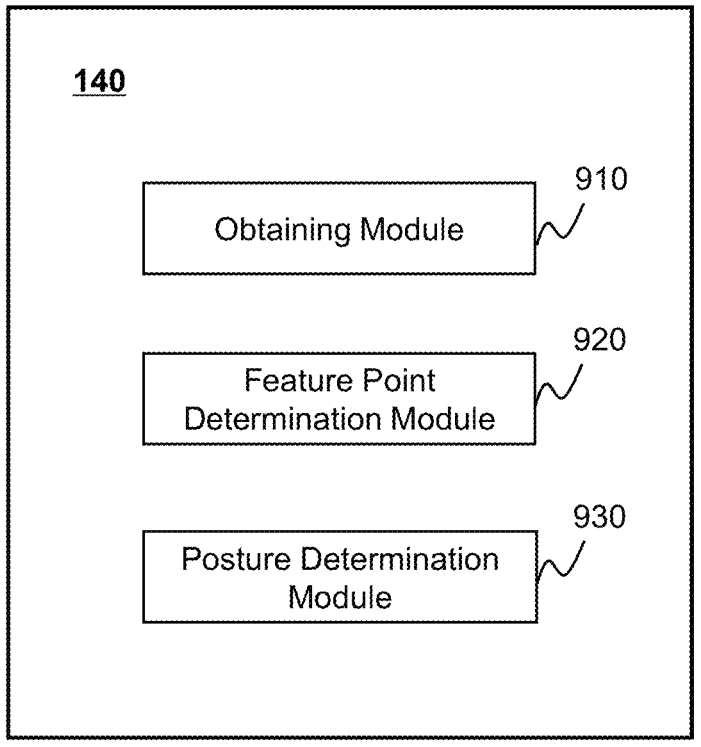
FIG. 9 is a block diagram illustrating an exemplary processor according to some embodiments of the present disclosure.

FIG. 9 is a block diagram illustrating an exemplary processor 102 according to some embodiments of the present disclosure. The processor 102 may include an obtaining module 910, a feature point determination module 920, and a posture determination module 930.

The obtaining module 910 may be configured to obtain a target image of a target object. The target image may include a 3D image (e.g., a depth image) and/or a 2D image of the target object. The target image may be captured using an image capturing apparatus. More descriptions regarding the obtaining the target image may be found in elsewhere in the present disclosure. See, e.g., operation 1002 in FIG. 10 and relevant descriptions thereof.

The feature point determination module 920 may be configured to determine at least one target feature point of the target object from the target image. A target feature point may represent a feature point of the target object in an image. In some embodiments, the feature point determination module 920 may also be configured to determine at least one reference feature point corresponding to the at least one target feature point from a reference model of the target object. The reference model may correspond to a target shooting angle. More descriptions regarding the determination of the at least one target feature point and the at least one reference feature point may be found in elsewhere in the present disclosure. See, e.g., operations 1004 and 1006 in FIG. 10 and relevant descriptions thereof.

The posture determination module 930 may be configured to determine a first target posture of the image capturing apparatus in a base coordinate system based on the at least one target feature point and the at least one reference feature point. In some embodiments, the first target posture may direct the image capturing apparatus to capture the target object from the target shooting angle and/or at a target shooting distance. More descriptions regarding the determination of the first target posture may be found in elsewhere in the present disclosure. See, e.g., operation 1008 in FIG. 10 and relevant descriptions thereof.

It should be noted that the descriptions of the robot control system and the modules thereof are provided for convenience of illustration, and are not intended to limit the scope of the present disclosure. It should be understood that those skilled in the art, having an understanding of the principles of the system, may arbitrarily combine the various modules or constitute subsystems connected to other modules without departing from the principles. For example, the obtaining module 910, the feature point determination module 920, and the posture determination module 930 disclosed in FIG. 9 may be different modules in the same system, or may be a single module that performs the functions of the modules mentioned above. As another example, modules of the robot control system may share a storage module, or each module may have an own storage module. As still another example, the obtaining module 910 and the obtaining module 210 may be the same module. Such modifications may not depart from the scope of the present disclosure.

In some embodiments, the processor 102 may further include a registration module configured to achieve registration between the target object and a planned image.

FIG. 10 is a flowchart illustrating an exemplary process 1000 for adjusting a posture of an image capturing apparatus according to some embodiments of the present disclosure. In some embodiments, the process 1000 may be implemented by the robot control system 100. For example, the process

1000 may be stored in a storage device (e.g., the storage 104) in the form of an instruction set (e.g., an application). In some embodiments, the processor 102 (e.g., the one or more modules as shown in FIG. 9) may execute the instruction set and direct one or more components of the robot control system 100 to perform the process 1000. In some embodiments, the adjustment of the posture of the image capturing apparatus described in operation 304 of FIG. 3 may be determined according to the process 1000.

In some embodiments, using a first image of a target object captured by the image capturing apparatus, the robot control system 100 may determine a surgical posture of the target object based on preoperative planning. By fixing the target object and adjusting the posture of the image capturing apparatus, a target region of the target object can be fully within a field of view of the image capturing apparatus.

At present, the image capturing apparatus is usually installed on a robot, and a doctor manually drags the image capturing apparatus to align with the target object. Since the doctor may not pay attention to physical characteristics of the image capturing apparatus during the drag process, it is difficult to adjust the image capturing apparatus quickly and accurately to an optimal posture, thereby reducing the efficiency of the shooting and the accuracy of the captured image data. In addition, the precision of the installation between the image capturing apparatus and the robot is reduced due to the drag of the image capturing apparatus by the doctor, further reducing the accuracy of the captured image data. Therefore, it is necessary to provide an effective system and method for adjusting the posture of the image capturing apparatus. In some embodiments, the posture of the image capturing apparatus may be adjusted by performing the following operations in the process 1000.

In 1002, the processor 102 (e.g., the obtaining module 910) may obtain a target image of a target object.

In some embodiments, the target object may include a biological object and/or a non-biological object. Merely by way of example, in a scenario of neurosurgery, the target object may be the head or face of a patient. The target image may include a 3D image (e.g., a depth image) and/or a 2D image of the target object. The target image may be captured using the image capturing apparatus. The target image is obtained may be in a similar manner to how the first image is obtained. More descriptions regarding the obtaining the target image may be found in elsewhere in the present disclosure. See, e.g., FIG. 3 and relevant descriptions thereof.

In 1004, the processor 102 (e.g., the feature point determination module 920) may determine at least one target feature point of the target object from the target image.

A target feature point may represent a feature point of the target object in an image. Merely by way of example, if the target object is the head or face of the patient, the at least one target feature point may be facial contour points of the target object as shown in FIG. 14. In some embodiments, the processor 102 may determine the at least one target feature point from the target image through a feature point extraction algorithm. For example, the processor 102 may determine the at least one target feature point from the target image through a feature point extraction model. More descriptions regarding the feature point extraction algorithm may be found in elsewhere in the present disclosure. See, e.g., operation 404 and relevant descriptions thereof.

In 1006, the processor 102 (e.g., the feature point determination module 920) may determine at least one reference feature point corresponding to the at least one target feature point from a reference model of the target object.

The reference model refers to a standard model that is constructed based on features of the target object. Merely by way of example, if the target object is the head or face of the patient, the reference model may be a standard human face model constructed based on head features of the human. Alternatively, the standard human face model may be downloaded from an open-source website. A front view and a side view of the standard human face model are shown in FIGS. 13A and 13B, respectively. In some embodiments, the reference model may be stored or displayed in the form of a 3D image, and the analysis and processing of the reference model may be performed based on the 3D image.

In some embodiments, the reference model may correspond to a target shooting angle. For example, the target shooting angle refers to an angle directly facing the target object. Merely by way of example, if the target object is the head or face of the patient, the target shooting angle may be an angle directly facing the face of the patient.

In some embodiments, each target feature point may correspond to a reference feature point. A target feature point and the corresponding reference feature point may correspond to a same physical point on the target object. The processor 102 may determine a corresponding reference feature point set from the reference model using the feature point extraction algorithm that is used to determine the at least one target feature point, and determine the reference feature point corresponding to each target feature point from the reference feature point set. In some embodiments, the processor 102 may determine at least one reference feature point from the reference model of the target object based on the at least one target feature point. For example, the processor 102 may determine the at least one reference feature point corresponding to the at least one target feature point based on a structural feature of the target object. As another example, the processor 102 may determine the at least one reference feature point corresponding to the at least one target feature point from the reference model of the target object using a machine learning model (e.g., a mapping model, an active appearance model (AAM), a Media-Pipe model, etc.). Merely by way of example, the processor 102 may input the target image and the reference model into the mapping model, and the mapping model may output a mapping relationship between points in the target image and points in the reference model. The processor 102 may determine the at least one reference feature point corresponding to the at least one target feature point based on the mapping relationship.

In 1008, the processor 102 (e.g., the posture determination module 930) may determine a first target posture of the image capturing apparatus in a base coordinate system based on the at least one target feature point and the at least one reference feature point.

The base coordinate system may be any coordinate system. In some embodiments, the base coordinate system refers to a coordinate system established based on a base of a robot. For example, the base coordinate system may be established with a center of a base bottom of the robot as an origin, the base bottom as an XY plane, and a vertical direction as a Z axis.

In some embodiments, the first target posture may reflect an adjusted posture of the image capturing apparatus in the base coordinate system. In some embodiments, the first target posture may direct the image capturing apparatus to capture the target object from the target shooting angle and/or at a target shooting distance. For example, the first target posture may be represented as a transformation relationship between a coordinate system (i.e., an updated first coordinate system) corresponding to the image capturing apparatus and the base coordinate system at the target shooting angle and target shooting distance. In some embodiments, the processor 102 may determine an initial posture of the target object relative to the image capturing apparatus based on the at least one target feature point and the at least one reference feature point. The processor 102 may determine a second target posture of the target object relative to the image capturing apparatus based on the initial posture. Further, the processor 102 may determine the first target posture of the image capturing apparatus in the base coordinate system based on the second target posture. More descriptions regarding the determination of the first target posture may be found in elsewhere in the present disclosure. See, e.g., FIG. 11 and relevant descriptions thereof.

In some embodiments, the image capturing apparatus may be installed on the robot. For example, the image capturing apparatus may be installed on an end terminal of a robotic arm of the robot. Therefore, the processor 102 may control the robot to move, so as to adjust the image capturing apparatus to the first target posture. In some embodiments, the processor 102 may determine a third target posture of the robot in the base coordinate system based on the first target posture. The processor 102 may control the robot to adjust to the third target posture, so as to adjust the image capturing apparatus to the first target posture. More descriptions regarding the determination of the third target posture may be found in elsewhere in the present disclosure. See, e.g., FIG. 12 and relevant descriptions thereof.

According to some embodiments of the present disclosure, the first target posture of the image capturing apparatus can be determined based on the at least one target feature point and the at least one reference feature point in the base coordinate system, so that the image capturing apparatus can shoot the target object at the target shooting angle and/or the target shooting distance. Therefore, the image capturing apparatus can be automatically positioned to the optimal position, which can improve the accuracy of the image data obtained by the image capturing apparatus, thereby improving the accuracy of subsequent robot positioning and preoperative planning.

It should be noted that the above descriptions of the process 1000 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the process 1000 may be accomplished with one or more additional operations not described, and/or without one or more of the operations discussed. For example, before capturing the target image of the target object, whether the field of view of the image capturing apparatus includes the target object may be determined. As another example, after adjusting the image capturing apparatus to the first target posture, image data (e.g., a first image) of the target object may be obtained for registering the target object with a planned image and/or positioning the robot.

FIG. 11 is a flowchart illustrating an exemplary process 1100 for determining a first target posture according to some embodiments of the present disclosure. In some embodiments, the process 1100 may be implemented by the robot control system 100. For example, the process 1100 may be stored in a storage device (e.g., the storage 104) in the form of an instruction set (e.g., an application). In some embodiments, the processor 102 (e.g., the one or more modules as shown in FIG. 9) may execute the instruction set and direct one or more components of the robot control system 100 to perform the process 1100. In some embodiments, the first target posture described in operation 1008 of FIG. 10 may be determined according to the process 1100.

In 1102, the processor 102 (e.g., the posture determination module 930) may determine an initial posture of a target object relative to an image capturing apparatus based on at least one target feature point and at least one reference feature point.

In some embodiments, the initial posture may be represented as a transformation relationship between a coordinate system corresponding to the target object and a first coordinate system corresponding to the image capturing apparatus when capturing a target image. In some embodiments, the initial posture may reflect the initial posture of the target object in the first coordinate system when the image capturing apparatus is at a target shooting angle, and/or an adjustment angle needed for adjusting the target object to a posture corresponding to the reference model in the first coordinate system.

In some embodiments, the processor 102 may transform the issue of determining the initial posture of the target object in the first coordinate system into solving a Perspective N Points (PNP) problem. The PNP problem refers to an object positioning problem that assumes that the image capturing apparatus is a pinhole model and has been calibrated, an image of N space points whose coordinates in the object coordinate system are known is taken, and coordinates of the N space points in the image are known, and the object positioning problem is used to determine the coordinates of the N space points in the first coordinate system corresponding to the image capturing apparatus.

Merely by way of example, the at least one target feature point may be facial contour points of the target object. After the facial contour points of the target object are determined, coordinates of the facial contour points in a coordinate system corresponding to the target object may be obtained. The coordinate system corresponding to the target object may be established based on the target object. Taking a human face as an example, the tip of the nose may be an origin of a face coordinate system, a plane parallel to the face may be an XY plane, and a direction perpendicular to the face may be a Z-axis. For example, if the target image is a 2D image, pixel coordinates corresponding to n determined facial contour points may be denoted as $A_i(x_i, y_i)$ (i=1, 2, 3, . . . , n), and spatial coordinates of n reference feature points in a reference model corresponding to the facial contour points in the coordinate system corresponding to the target object may be denoted as $B_j(X_j, Y_j, Z_j)$ (j=1, 2, 3, . . . n). The initial posture $_{face}{}^{camera}$T of the target object relative to the image capturing apparatus before the posture adjustment (also referred to as a posture transformation matrix $_{face}{}^{camera}$T from the coordinate system corresponding to the target object to the first coordinate system) may be determined according to Equation (1):

$$\begin{bmatrix} x_i \\ y_i \\ 1 \end{bmatrix} = M_{face}^{camera}T \begin{bmatrix} X_j \\ Y_j \\ Z_j \end{bmatrix} (i = j = 1, 2, 3 \ldots n), \tag{1}$$

where M refers to a parameter matrix of the image capturing apparatus, which may be determined based on intrinsic parameter(s) of the image capturing apparatus.

As another example, if the target image is a 3D image, pixel coordinates corresponding to n determined facial contour points may be denoted as $A_i(x_i, y_i, z_i)$ (i=1, 2, 3, . . . , n), and spatial coordinates of n reference feature points in a reference model corresponding to the facial contour points in the coordinate system corresponding to the target object may be denoted as $B_j(X_j, Y_j, Z_j)$ (j=1, 2, 3, . . . , n). The initial posture $_{face}{}^{camera}$T of the target object relative to the image capturing apparatus before the posture f ace adjustment (also referred to as a posture transformation matrix $_{face}{}^{camera}$T from the coordinate system corresponding to the target object to the first coordinate system) may be determined according to Equation (2):

$$\begin{bmatrix} x_i \\ y_i \\ z_i \end{bmatrix} = M_{face}^{camera}T \begin{bmatrix} X_j \\ Y_j \\ Z_j \end{bmatrix} (i = j = 1, 2, 3 \ldots n). \tag{2}$$

Through the above operation, the angle needed for adjusting the target object to the posture corresponding to the reference model in the first coordinate system may be determined based on the at least one target feature point, the at least one reference feature point, and the parameter matrix of the image capturing apparatus.

In 1104, the processor 102 (e.g., the posture determination module 930) may determine a second target posture of the target object relative to the image capturing apparatus based on the initial posture.

The second target posture may be represented as a transformation relationship between the coordinate system corresponding to the target object and an updated first coordinate system corresponding to the adjusted image capturing apparatus. In some embodiments, the second target posture may reflect a posture of the target object in the updated first coordinate system after adjusting the posture of the image capturing apparatus (e.g., adjusting to the target shooting angle and the target shooting distance), and/or a distance needed for adjusting a shooting distance to the target shooting distance in the updated first coordinate system.

The target shooting distance refers to a distance in a height direction between the target object and the image capturing apparatus when the quality of the image data captured by the image capturing apparatus meets a preset standard. In some embodiments, the processor 102 may obtain the target shooting distance of the image capturing apparatus. For example, the target shooting distance may be predetermined and stored in a storage device (e.g., the storage 104), and the processor 102 may retrieve the target shooting distance from the storage device. Merely by way of example, when the whole target object (or other reference objects, such as a facial model) is displayed within the field of view of the image capturing apparatus, the image capturing apparatus may be moved along a direction of an optical axis of the image capturing apparatus to capture image data of the target object at a plurality of shooting distances. The processor 102 may determine an optimal shooting distance between the target object and the image capturing apparatus based on the accuracy and quality (e.g., definition) of the image data at each of the plurality of shooting distances, and determine the optimal shooting distance as the target shooting distance. In some embodiments, the target shooting distance of the image capturing apparatus may be determined through marker points. For example, a plurality of marker points may be disposed on the target object, and coordinates of the plurality of marker points may be determined as standard coordinates through a high-precision image capturing device. The processor 102 may determine coordinates of the plurality of marker points at the different shooting distances, respectively, by capturing the plurality of marker points at different shooting distances using the image capturing apparatus. The processor 102 may compare the coordinates determined at the different shooting distances with the standard coordinates, and determine a shooting distance corresponding to coordinates with a minimum deviation from the standard coordinates as the target shooting distance.

In some embodiments, the processor 102 may determine a distance transformation matrix based on the target shooting distance. Merely by way of example, if the target shooting distance is H, the distance transformation matrix P may be represented as shown in Equation (3):

$$P = \begin{bmatrix} 1 & 0 & 0 & 0 \\ 0 & 1 & 0 & 0 \\ 0 & 0 & 1 & H \\ 0 & 0 & 0 & 1 \end{bmatrix}. \tag{3}$$

In some embodiments, the processor 102 may determine the second target posture (i.e., a target posture of the target object relative to the image capturing apparatus after the posture adjustment) of the target object in the updated first coordinate system at the target shooting distance based on the distance transformation matrix and the initial posture. For example, the second target posture may be determined according to Equation (4):

$$_{face}^{camera}T' = _{face}^{camera}T \times \begin{bmatrix} 1 & 0 & 0 & 0 \\ 0 & 1 & 0 & 0 \\ 0 & 0 & 1 & H \\ 0 & 0 & 0 & 1 \end{bmatrix}, \tag{4}$$

where $_{face}^{camera}T$ refers to the initial posture of the target object in the first coordinate system before the update, and $_{face}^{camera}T'$ refers to the second target posture of the target object in the updated first coordinate system at the target shooting distance.

By determining the second target posture of the target object in the updated first coordinate system at the target shooting distance, the shooting distance between the target object and the image capturing apparatus can be adjusted to the target shooting distance, thereby improving the accuracy of the image data captured by the image capturing apparatus.

In 1106, the processor 102 (e.g., the posture determination module 930) may determine a first target posture of the image capturing apparatus in a base coordinate system based on the second target posture of the target object relative to the image capturing apparatus.

In some embodiments, the image capturing apparatus may be installed on a robot. Therefore, a fourth transformation relationship between the first coordinate system and the base coordinate system may be determined through a connection structure between the image capturing apparatus and the robot. Further, the processor 102 may determine the first target posture based on the fourth transformation relationship and the second target posture.

Merely by way of example, the processor 102 may obtain a first transformation relationship between the first coordinate system and a second coordinate system corresponding to the robot. The first transformation relationship refers to a mapping relationship between a position of the robot and a position of the image capturing apparatus. More descriptions regarding the obtaining the first transformation relationship may be found in elsewhere in the present disclosure. See, e.g., FIG. 3 and relevant descriptions thereof. The processor 102 may also obtain a fifth transformation relationship between the second coordinate system and the base coordinate system. In some embodiments, the processor 102 may determine the fifth transformation relationship through a preset calibration technique (e.g., a hand-eye calibration technique). For example, the processor 102 may determine the fifth transformation relationship in a similar manner to how the first transformation relationship is determined. In some embodiments, the fifth transformation relationship may be a parameter of the robot, and the processor 102 may retrieve the fifth transformation relationship from a controller of the robot. Further, the processor 102 may determine the fourth transformation relationship based on the first transformation relationship and the fifth transformation relationship. Merely by way of example, the fourth transformation relationship may be determined according to Equation (5):

$$T = _{camera}^{tool}T \times _{tool}^{base}T, \tag{5}$$

wherein T refers to the fourth transformation relationship between the first coordinate system corresponding to the image capturing apparatus and the base coordinate system, $_{camera}^{tool}T$ refers to the first transformation relationship between the first coordinate system corresponding to the image capturing apparatus and the second coordinate system corresponding to the robot, and $_{tool}^{base}T$ refers to the fifth transformation relationship between the second coordinate system corresponding to the robot and the base coordinate system.

In some embodiments, the processor 102 may determine the first target posture based on the fourth transformation relationship and the second target posture. Merely by way of example, the first target posture may be determined according to Equation (6):

$$_{camera}^{base}T' = _{face\_link\_view}^{base}T = _{face}^{camera}T' \times _{camera}^{tool}T \times _{tool}^{base}T, \tag{6}$$

where $_{camera}^{base}T'$ and $_{face\_link\_view}^{base}T$ refer to the first target posture.

According to some embodiments of the present disclosure, by determining the fourth transformation relationship between the first coordinate system corresponding to the image capturing apparatus and the base coordinate system, the first target posture of the target object in the base coordinate system can be determined based on the fourth transformation relationship and the second target posture of the target object in the updated first coordinate system, which can adjust the image capturing apparatus to the target shooting angle and the target shooting distance, thereby improving the accuracy of the captured image data.

It should be noted that the above descriptions of the process 1100 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the process 1100 may be accomplished with one or more additional operations not described, and/or without one or more of the operations discussed.

FIG. 12 is a flowchart illustrating an exemplary process 1200 for adjusting a posture of an image capturing apparatus according to some embodiments of the present disclosure. In some embodiments, the process 1200 may be implemented by the robot control system 100. For example, the process 1200 may be stored in a storage device (e.g., the storage 104) in the form of an instruction set (e.g., an application). In some embodiments, the processor 102 (e.g., the one or more modules as shown in FIG. 9) may execute the instruction set and direct one or more components of the robot control system 100 to perform the process 1200.

In some embodiments, an image capturing apparatus may be installed on a robot. For example, the image capturing apparatus may be installed at an end terminal of a robotic arm of the robot. The process 1200 may be performed after operation 1008 described in FIG. 10, so that the robot control system 100 can control the movement of the robot to adjust the image capturing apparatus to the first target posture.

In 1202, the processor 102 (e.g., the posture determination module 930) may determine a third target posture of a robot in a base coordinate system based on a first target posture.

In some embodiments, the third target posture may reflect a posture of the robot in the base coordinate system when the image capturing apparatus is in the first target posture, and/or a distance and an angle that the robot needs to move in the base coordinate system to adjust the image capturing apparatus to the first target posture. In some embodiments, the third target posture may be represented as a transformation relationship between a second coordinate system corresponding to the robot and the base coordinate system when the image capturing apparatus is in the first target posture.

In some embodiments, the processor 102 may determine the third target posture of the robot in the base coordinate system based on a first transformation relationship and the first target posture. Merely by way of example, the third target posture may be determined according to Equation (7):

$$_{tool}^{base}T' = _{camera}^{base}T \times (_{camera}^{tool}T)^{-1}, \tag{7}$$

where $_{base}^{tool}T$ refers to the third target posture.

In 1204, the processor 102 (e.g., the posture determination module 930) may cause the robot to adjust to the third target posture, so as to adjust the image capturing apparatus to the first target posture.

Merely by way of example, referring to FIGS. 16A to 16H, FIG. 16A is a schematic diagram illustrating an image capturing apparatus before posture adjustment according to some embodiments of the present disclosure. FIG. 16B is a schematic diagram illustrating an image capturing apparatus after posture adjustment according to some embodiments of the present disclosure. FIGS. 16C, 16E, and 16G are schematic diagrams illustrating image data captured by an image capturing apparatus before posture adjustment according to some embodiments of the present disclosure. FIGS. 16D, 16F, and 16H are schematic diagrams illustrating image data captured by an image capturing apparatus after posture adjustment according to some embodiments of the present disclosure. Combining FIGS. 16A and 16B, by causing a robot to adjust to a third target posture, an image capturing apparatus 1610 is adjusted from a posture as shown in FIG. 16A to a first target posture as shown in FIG. 16B. Comparing FIGS. 16C and 16D, FIGS. 16E and 16F, and FIGS. 16G and 16H, it may be determined that imaging positions of target objects 1620, 1630, and 1640 in image data are adjusted to a center of the image data, respectively, after the image capturing apparatus is adjusted to the first target posture. In other words, after the image capturing apparatus is adjusted to the first target posture, the image capturing apparatus can capture the image data of the target objects at a target shooting angle and a target shooting height.

According to some embodiments of the present disclosure, the posture (i.e., the third target posture) of the robot in the base coordinate system can be determined accurately, thereby accurately adjusting the posture of the image capturing apparatus based on the posture of the robot in the base coordinate system. Therefore, the image capturing apparatus can capture the image data of the target objects at the target shooting angle and the target shooting distance, thereby improving the accuracy of the captured image data.

It should be noted that the above descriptions of the process 1200 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the process 1200 may be accomplished with one or more additional operations not described, and/or without one or more of the operations discussed.

FIGS. 15A to 15C are schematic diagrams illustrating an exemplary process for adjusting a posture of an image capturing apparatus 1510 according to some embodiments of the present disclosure.

After the image capturing apparatus 1510 is installed, a robot may be located at a random initial position. As shown in FIG. 15A, a field of view of the image capturing apparatus 1510 does not include the face of a patient (i.e., a target object). Therefore, the posture of the robot needs to be adjusted locally first, so that the field of view of the image capturing apparatus 1510 displays the whole or partial face of the patient. Merely by way of example, before capturing a target image of the target object, the robot control system 100 may determine whether the field of view of the image capturing apparatus 1510 includes at least one target feature point. In response to determining that the field of view of the image capturing apparatus 1510 includes the at least one target feature point, the robot control system 100 may capture the target image of the target object using the image capturing apparatus 1510. In response to determining that the field of view of the image capturing apparatus 1510 does not include the at least one target feature point, the robot control system 100 may adjust the image capturing apparatus 1510, so that the field of view of the image capturing apparatus 1510 includes the at least one target feature point.

When the field of view of the image capturing apparatus 1510 includes the at least one target feature point (as shown in FIG. 15B), the robot control system 100 (e.g., the processor 102) may execute a process for adjusting a posture of the image capturing apparatus as illustrated in FIGS. 10 to 12, so that the image capturing apparatus 1510 can capture image data of the target object from a target shooting angle and a target shooting distance (as shown in FIG. 15C).

By adjusting the image capturing apparatus to include at least a portion of the target object in the field of view of the image capturing apparatus before capturing the target image, the efficiency of adjusting the posture of the image capturing apparatus can be improved.

FIG. 17 is a schematic diagram illustrating an exemplary posture adjustment process of an image capturing apparatus according to some embodiments of the present disclosure.

As shown in FIG. 17, a first coordinate system corresponding to an image capturing apparatus when capturing a target image is camera_link, a coordinate system corresponding to a target object is face_link, an updated first coordinate system of the image capturing apparatus at a target shooting distance is face_link_view, a second coordinate system corresponding to a robot is tool_link, and a base coordinate system is base_link.

An initial posture $_{face}{}^{camera}\mathrm{T}$ of the target object in the first coordinate system camera_link may be determined, based on at least one target feature point and at least one reference feature point, using Equation (1) or Equation (2). A second target posture $_{face}{}^{camera}\mathrm{T'}$ of the target object in the updated first coordinate system face_link_view at the target shooting distance may be determined using Equation (4). By obtaining a first transformation relationship $_{camera}{}^{tool}\mathrm{T}$ between the first coordinate system camera_link and the second coordinate system tool_link and obtaining a fifth transformation relationship $_{tool}{}^{base}\mathrm{T}$ between the second coordinate system tool_link and the base coordinate system base_link, a fourth transformation relationship T between the first coordinate system camera_link and the base coordinate system base_link may be determined using Equation (5). The first target posture $_{camera}{}^{base}\mathrm{T'}$ may be determined, based on the fourth transformation relationship T and the second target posture $_{face}{}^{camera}\mathrm{T'}$, using Equation (6).

In some embodiments, a third target posture of the robot in the base coordinate system may be determined, based on an inverse operation $(_{camera}{}^{tool}\mathrm{T})^{-1}$ of the first transformation relationship and the first target posture $_{camera}{}^{base}\mathrm{T'}$, using Equation (7). Merely by way of example, $_{tool}{}^{base}\mathrm{T'}$ may be determined using Equation (7).

FIG. 18 is a schematic diagram illustrating an exemplary robot control system 1800 according to some embodiments of the present disclosure.

As shown in FIG. 18, the robot control system 1800 may include a robot 1810, an image capturing apparatus 1820, and a processor 1830. The image capturing apparatus 1820 may be installed on the robot 1810 (e.g., at an end terminal of a robotic arm of the robot). The processor 1830 may be connected to the robot 1810 and the image capturing apparatus 1820, respectively. When the processor 1830 operates, the processor 1830 may execute the robot positioning process and the posture adjustment process of the image capturing apparatus as described in some embodiments of the present disclosure.

In one embodiment, a computer device is provided. The computer device may be a server, and an internal structure diagram of the computer device may be as shown in FIG. 19. The computer device includes a processor, a storage, a communication interface, a display screen, and an input device connected via a system bus. The processor of the computer device is configured to provide computation and control capabilities. For example, the processor of the computer device may execute the robot positioning method and posture adjustment method of image capturing apparatus as described in some embodiments of the present disclosure. The storage of the computer device includes a non-volatile storage medium and an internal memory. The non-volatile storage medium stores an operating system and a computer program. The internal memory provides an environment for running the operating system and the computer program stored in the non-volatile storage medium. The communication interface of the computer device is used for wired or wireless communication with an external terminal. The wireless communication may be achieved through techniques, such as Wi-Fi, a cellular network, a near field communication (NFC), etc. The computer program is executed by the processor to implement the robot positioning method. The display screen of the computer device may include an LCD screen or an e-ink display screen. The input device of the computer device may include a touch layer overlaid on the display screen, a physical button, a trackball, or a touchpad on the housing of the computer device, or an external device such as a keyboard, a touchpad, a mouse, etc.

It should be understood by those skilled in the art that the structure shown in FIG. 19 is merely a block diagram of a partial structure related to the embodiments of the present disclosure, and does not constitute a limitation on the computer device to which the embodiments of the present disclosure are applied. A specific computer device may include more or fewer parts than the structure shown in the FIG. 19, or combine certain components, or include a different arrangement of components.

FIG. 20 is a flowchart illustrating an exemplary robot control process 2000 according to some embodiments of the present disclosure. In some embodiments, the process 2000 may be implemented by the robot control system 100. For example, the process 2000 may be stored in a storage device (e.g., the storage 104) in the form of an instruction set (e.g., an application). In some embodiments, the processor 102 (e.g., the one or more modules as shown in FIG. 2 and/or the one or more modules shown in FIG. 9) may execute the instruction set and direct one or more components of the robot control system 100 to perform the process 2000.

In 2002, the processor 102 may capture a target image of a target object using an image capturing apparatus.

In 2004, the processor 102 may determine at least one target feature point of the target object from the target image.

In 2006, the processor 102 may determine at least one reference feature point corresponding to the at least one target feature point from a reference model of the target object. The reference model may correspond to a target shooting angle.

In 2008, the processor 102 may determine a first target posture of the image capturing apparatus in a base coordinate system based on the at least one target feature point and the at least one reference feature point, such that the image capturing apparatus can shoot the target object from the target shooting angle.

In 2010, the processor 102 may obtain a first image and a second image of the target object. The first image may be captured using an adjusted image capturing apparatus, and the second image may be captured using a medical imaging device.

In 2012, the processor 102 may determine at least one target region corresponding to at least one target portion of the target object from the first image. The at least one target portion may be less affected by physiological motions than other portions.

In 2014, the processor 102 may determine positioning information of the robot based on the at least one target region and the second image.

According to some embodiments of the present disclosure, a posture adjustment may be performed on the image capturing apparatus, and then a positioning operation is performed on the robot. The image capturing apparatus after the posture adjustment can capture the first image at the target shooting angle and the target shooting distance, which can improve the accuracy of the first image, thereby improving the accuracy of the robot positioning, and the accuracy of preoperative planning or surgical operations.

It should be noted that the above descriptions of the process 2000 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the process 1000 may be accomplished with one or more additional operations not described, and/or without one or more of the operations discussed. For example, the processor 102 may further perform the registration between the target object and the planning image based on the first image, thereby improving the accuracy of the registration plan According to some embodiments of the present disclosure, (1) by determining the first target posture of the image capturing apparatus in the base coordinate system based on the at least one target feature point and the at least one reference feature point, the image capturing apparatus can shoot the target object at the target shooting angle and/or the target shooting distance, which can result in automatic positioning of the image capturing apparatus to the optimal position, thereby improving the accuracy of the image data captured by the image capturing apparatus and the accuracy of the registration plan; (2) by capturing the first image using the adjusted image capturing apparatus, the accuracy of the first image can be improved, thereby improving the accuracy of the robot positioning; (3) by determining the transformation relationships between the coordinate systems of the robot, the image capturing apparatus, and the medical imaging device based on the target region in the first image and the second image, no additional markers need to be attached to or disposed on the target object, avoiding additional harm to the target object; (4) by performing the robot positioning based on the medical image, the accuracy of the robot positioning can be improved, thereby improving the accuracy of preoperative planning or surgical operations.

Some embodiments of the present disclosure further provide an electronic device. The electronic device includes at least one storage medium storing computer instructions, and at least one processor. When the at least one processor executes the computer instructions, the robot positioning method and the posture adjustment method of image capturing apparatus described in the present disclosure may be implemented. The electronic device may also include a transmission device and an input/output device. The transmission device and the input/output device may be connected to the at least one processor. More descriptions regarding the techniques may be found in elsewhere in the present disclosure. See, e.g., FIGS. 1A to 17, and relevant descriptions thereof.

Some embodiments of the present disclosure further provide a non-transitory computer-readable storage medium that stores the computer instruction. When reading the instruction, a computer may execute the robot positioning method and the posture adjustment method of image capturing apparatus described in the present disclosure. More descriptions regarding the techniques may be found in elsewhere in the present disclosure. See, e.g., FIGS. 1A to 17, and relevant descriptions thereof.

The basic concepts have been described above, and it will be apparent to those skilled in the art that the foregoing detailed disclosure is intended as an example only and does not constitute a limitation of the present disclosure. Although not expressly stated herein, a person skilled in the art may make various modifications, improvements, and amendments to the present disclosure. Such modifications, improvements, and amendments are suggested in the present disclosure, so such modifications, improvements, and amendments remain within the spirit and scope of the exemplary embodiments of the present disclosure.

Also, the present disclosure uses specific words to describe the embodiments of the present disclosure. For example, "an embodiment," "one embodiment," and/or "some embodiments" means a feature, structure, or characteristic related to at least one embodiment of the present disclosure. Accordingly, it should be emphasized and noted that "an embodiment," "one embodiment," or "an alternative embodiment" referred to two or more times in different places in the present disclosure do not necessarily refer to the same embodiment. In addition, certain features, structures, or characteristics of one or more embodiments of the present disclosure may be suitably combined.

Furthermore, unless explicitly stated in the claims, the order of processing elements and sequences, the use of numerical and alphabetic characters, or the use of other names in the present disclosure are not intended to limit the sequence of the processes and methods described herein. While various examples have been discussed in the present disclosure to illustrate certain inventive embodiments that are currently considered useful, it should be understood that such details are provided for illustrative purposes and that the appended claims are not limited to the disclosed embodiments. Instead, the claims are intended to cover all modifications and equivalent combinations that fall within the spirit and scope of the embodiments described in the present disclosure. For example, while the system components described above may be implemented through hardware devices, they may also be achieved solely through software solutions, such as by installing the described system on existing servers or mobile devices.

Similarly, it should be noted that in order to simplify the presentation of the present disclosure, and thereby aid in the understanding of one or more embodiments, the preceding description of embodiments of the present disclosure sometimes incorporates a variety of features into a single embodiment, accompanying drawings, or description thereof. However, this manner of disclosure does not imply that the subject matter of the present disclosure requires more features than those mentioned in the claims. Rather, claimed subject matter may lie in less than all features of a single foregoing disclosed embodiment.

Some embodiments use numbers to describe the number of components, and attributes, and it should be understood that such numbers used in the description of the embodiments are modified in some examples by the modifiers "about," "approximately," or "generally." Unless otherwise stated, "about," "approximately," or "generally" indicates that a variation of ±20% is permitted. Accordingly, in some embodiments, the numerical parameters used in the present disclosure and claims are approximations, which may change depending on the desired characteristics of the individual embodiment. In some embodiments, the numeric parameters should be considered with the specified significant figures and be rounded to a general number of decimal places. Although the numerical domains and parameters configured to confirm the breadth of their ranges in some embodiments of the present disclosure are approximations, in specific embodiments such values are set as precisely as possible within the feasible range.

With respect to each patent, patent application, patent application disclosure, and other material, such as articles, books, manuals, publications, documents, etc., cited in the present disclosure, the entire contents thereof are hereby incorporated herein by reference. Application history documents that are inconsistent with or conflict with the contents of the present disclosure are excluded, as are documents (currently or hereafter appended to the present disclosure) that limit the broadest scope of the claims of the present disclosure. It should be noted that in the event of any inconsistency or conflict between the descriptions, definitions, and/or use of terminology in the materials appended to the present disclosure and those described in the present disclosure, the descriptions, definitions, and/or use of terminology in the present disclosure shall prevail.

In closing, it should be understood that the embodiments described in the present disclosure are intended only to illustrate the principles of the embodiments of the present disclosure. Other deformations may also fall within the scope of the present disclosure. Thus, by way of example and not limitation, alternative configurations of embodiments of the present disclosure may be considered consistent with the teachings of the present disclosure. Accordingly, the embodiments of the present disclosure are not limited to the embodiments expressly presented and described herein.

What is claimed is:

1. A method for positioning a robot, comprising:
causing the robot to adjust an image capturing apparatus installed on the robot to a first target posture;
obtaining a first image and a second image including a face of a target object, the first image being captured using the image capturing apparatus at the first target posture, and the second image being captured using a medical imaging device;
determining at least one target region corresponding to at least one target portion of the target object from the first image, wherein the at least one target portion is a static facial region that is less affected by changes in facial expressions than other facial portions; and
determining positioning information of the robot based on the at least one target region and the second image.

2. The method of claim 1, wherein the determining at least one target region corresponding to at least one target portion of the target object from the first image includes:
obtaining a two-dimensional (2D) reference image of the target object captured using the image capturing apparatus;
determining at least one reference region corresponding to the at least one target portion from the 2D reference image; and
determining the at least one target region from the first image based on the at least one reference region.

3. The method of claim 1, wherein the determining positioning information of the robot based on the at least one target region and the second image includes:
obtaining a first transformation relationship between a first coordinate system corresponding to the image capturing apparatus and a second coordinate system corresponding to the robot;
determining a second transformation relationship between the first coordinate system and a third coordinate system corresponding to the medical imaging device based on a registration relationship between the at least one target region and the second image; and
determining the positioning information of the robot based on the first transformation relationship and the second transformation relationship.

4. The method of claim 3, further comprising:
determining at least one reference point from the second image;
determining at least one target point corresponding to the at least one reference point from the at least one target region; and
determining the registration relationship between the at least one target region and the second image based on a corresponding relationship between the at least one reference point and the at least one target point.

5. The method of claim 4, wherein the at least one reference point forms at least one reference point set, each of the at least one reference point set includes at least three reference points located on a same plane, and
the determining at least one target point corresponding to the at least one reference point from the at least one target region includes:
for each reference point set in the at least one reference point set, determining a positional relationship between reference point pairs in the reference point set;
determining a target point set corresponding to the reference point set from the at least one target region, the target point set including at least three target points located on a same plane based on the positional relationship; and
determining a target point corresponding to each reference point in the reference point set based on the target point set.

6. The method of claim 5, wherein for each reference point set in the at least one reference point set, the determining a target point set corresponding to the reference point set from the at least one target region includes:
determining a distance and a direction between each two reference points among the reference point set based on coordinates of the at least three reference points in the reference point set;
determining vector information of the reference point set based on the distance and the direction between each two reference points among the reference point set; and
determining the target point set corresponding to the reference point set from the at least one target region based on the vector information of the reference point set.

7. The method of claim 6, wherein the determining the target point set corresponding to the reference point set from the at least one target region based on the vector information of the reference point set includes:
determining a first distance between each two reference points among the reference point set based on the vector information of the reference point set;
determining a second distance between each two candidate target points among each of a plurality of candidate target point sets in the at least one target region;
determining a deviation between each first distance and the corresponding second distance; and
determining the target point set corresponding to the reference point set from the plurality of candidate target point sets based on the deviation between each first distance and the corresponding second distance.

8. The method of claim 4, wherein the determining the registration relationship between the at least one target region and the second image based on a corresponding relationship between the at least one reference point and the at least one target point includes:
determining an initial registration relationship between the at least one target region and the second image based on the corresponding relationship between the at least one reference point and the at least one target point; and
determining the registration relationship by adjusting the initial registration relationship using an iterative closest point (ICP) algorithm.

9. The method of claim 1, wherein the first target posture is determined by:
obtaining a target image and a reference model of the target object, wherein the target image is captured using the image capturing apparatus with an initial posture, and the reference model referring to a standard model that is constructed based on features of the target object;

determining the first target posture of the image capturing apparatus in a base coordinate system based on the target image and the reference model.

10. The method of claim 9, wherein the determining the first target posture of the image capturing apparatus in a base coordinate system based on the target image and the reference model includes:

determining at least one target feature point of the target object from the target image;

determining at least one reference feature point corresponding to the at least one target feature point from the reference model; and determining the first target posture of the image capturing apparatus in the base coordinate system based on the at least one target feature point and the at least one reference feature point.

11. The method of claim 10, wherein the determining the first target posture of the image capturing apparatus in the base coordinate system based on the at least one target feature point and the at least one reference feature point includes:

determining the initial posture of the target object relative to the image capturing apparatus based on the at least one target feature point and the at least one reference feature point;

determining a second target posture of the target object relative to the image capturing apparatus based on the initial posture; and determining the first target posture based on the second target posture.

12. The method of claim 11, wherein the determining the first target posture based on the second target posture includes:

determining a transformation relationship between a first coordinate system corresponding to the image capturing apparatus and the base coordinate system; and determining the first target posture based on the transformation relationship between the first coordinate system and the base coordinate system, and the second target posture.

13. The method of claim 12, wherein the determining a transformation relationship between a first coordinate system corresponding to the image capturing apparatus and the base coordinate system includes:

obtaining a transformation relationship between the first coordinate system and a second coordinate system corresponding to the robot;

obtaining a transformation relationship between the second coordinate system and the base coordinate system; and determining the transformation relationship between the first coordinate system and the base coordinate system based on the transformation relationship between the first coordinate system and the second coordinate system, and the transformation relationship between the second coordinate system and the base coordinate system.

14. The method of claim 1, wherein the causing the robot to adjust an image capturing apparatus installed on the robot to a first target posture comprises:

determining a third target posture of the robot in a base coordinate system based on the first target posture; and causing the robot to adjust to the third target posture, so as to adjust the image capturing apparatus to the first target posture.

15. The method of claim 1, wherein the static facial region is determined based on physiological structure information or determined by:

capturing shape data of human faces under different facial expressions;

obtaining a region that is less affected by the changes in facial expressions by performing a statistical analysis on the shape data; and determining the region as the static facial region.

16. The method of claim 1, wherein the first target posture is determined by:

obtaining a target image and a reference model of the target object, wherein the target image is captured using the image capturing apparatus with an initial posture, and the reference model referring to a standard model that is constructed based on features of the target object;

determining a second target posture of the target object relative to the image capturing apparatus based on the initial posture;

determining a transformation relationship between a first coordinate system corresponding to the image capturing apparatus and a base coordinate system; and determining the first target posture based on the second target posture and the transformation relationship.

17. The method of claim 16, wherein the reference model corresponds to a target shooting angle, the target shooting angle referring to an angle directly facing the face of the target object, and the first target posture directs the image capturing apparatus to capture the target object from the target shooting angle.

18. The method of claim 16, wherein the first target posture further directs the image capturing apparatus to capture the target object at a target shooting distance, and the determining a second target posture of the target object relative to the image capturing apparatus based on the initial posture comprises:

determining a distance transformation matrix based on the target shooting distance; and determining the second target posture based on the distance transformation matrix and the initial posture.

19. A system for positioning a robot, comprising:

a storage device, configured to store a computer instruction; and a processor connected to the storage device, wherein when executing the computer instruction, the processor causes the system to perform the following operations:

causing the robot to adjust an image capturing apparatus installed on the robot to a first target posture;

obtaining a first image and a second image including a face of a target object, the first image being captured using the image capturing apparatus at the first target posture, and the second image being captured using a medical imaging device;

determining at least one target region corresponding to at least one target portion of the target object from the first image, wherein the at least one target portion is a static facial region that is less affected by changes in facial expressions than other facial portions; and determining positioning information of the robot based on the at least one target region and the second image.

20. A non-transitory computer readable medium, comprising executable instructions that, when executed by at least one processor, direct the at least one processor to perform a method, the method comprising:

causing a robot to adjust an image capturing apparatus installed on the robot to a first target posture;

obtaining a first image and a second image including a face of a target object, the first image being captured using the image capturing apparatus at the first target posture, and the second image being captured using a medical imaging device;

determining at least one target region corresponding to at least one target portion of the target object from the first image, wherein the at least one target portion is a static facial region that is less affected by changes in facial expressions than other facial portions; and determining positioning information of the robot based on the at least one target region and the second image.

\* \* \* \* \*